(12) United States Patent
Meskens et al.

(10) Patent No.: US 12,011,593 B2
(45) Date of Patent: **\*Jun. 18, 2024**

(54) ACOUSTIC OUTPUT DEVICE WITH ANTENNA

(71) Applicant: Cochlear Limited, Macquarie University (AU)

(72) Inventors: Werner Meskens, Opwijk (BE); Tadeusz Jurkiewicz, Rozelle (AU); Steve Winnall, Stanmore (AU); Limin Zhong, Denistone (AU)

(73) Assignee: Cochlear Limited, Macquarie University (AU)

( * ) Notice: Subject to any disclaimer, the term of this patent is extended or adjusted under 35 U.S.C. 154(b) by 0 days.

This patent is subject to a terminal disclaimer.

(21) Appl. No.: 18/456,130

(22) Filed: Aug. 25, 2023

(65) Prior Publication Data

US 2023/0398354 A1    Dec. 14, 2023

Related U.S. Application Data

(60) Division of application No. 17/844,960, filed on Jun. 21, 2022, now Pat. No. 11,819,690, which is a
(Continued)

(51) Int. Cl.
*A61N 1/36* (2006.01)
*H04R 25/00* (2006.01)

(52) U.S. Cl.
CPC ....... *A61N 1/36036* (2017.08); *H04R 25/554* (2013.01); *H04R 25/556* (2013.01);
(Continued)

(58) Field of Classification Search
CPC ............ A61N 1/36036; H04R 25/554; H04R 25/556; H04R 25/60; H04R 25/65; H04R 25/607; H04R 2225/0216; H04R 2225/025; H04R 2225/51; H04R 2225/55; H04R 2225/57
See application file for complete search history.

(56) References Cited

U.S. PATENT DOCUMENTS 2,535,063 A    12/1950   Halstead
2,573,438 A    10/1951   Hathaway et al.
(Continued)

FOREIGN PATENT DOCUMENTS

CN    1684549 A      10/2005
CN    101835082 A    9/2010
(Continued)

OTHER PUBLICATIONS

1st Technical Examination and Search Report dated Jan. 25, 2013 for DK Patent Application No. PA 2012 70412, 4 pages.
(Continued)

*Primary Examiner* — Amanda K Hulbert
*Assistant Examiner* — Natasha Patel
(74) *Attorney, Agent, or Firm* — Edell, Shapiro & Finnan, LLC

(57) ABSTRACT

A hearing device is provided. The hearing device comprises a first portion configured to be arranged at a head of a user and to provide a signal to a second portion.

18 Claims, 16 Drawing Sheets

Related U.S. Application Data continuation of application No. 17/565,676, filed on Dec. 30, 2021, now Pat. No. 11,491,331, which is a continuation of application No. 17/405,287, filed on Aug. 18, 2021, which is a continuation of application No. 16/274,363, filed on Feb. 13, 2019, now Pat. No. 11,123,559, which is a continuation of application No. 15/188,780, filed on Jun. 21, 2016, now Pat. No. 10,219,084, which is a continuation of application No. 14/199,263, filed on Mar. 6, 2014, now Pat. No. 9,446,233, which is a continuation of application No. 12/131,867, filed on Jun. 2, 2008, now Pat. No. 8,934,984.

(60) Provisional application No. 60/924,800, filed on May 31, 2007, provisional application No. 60/924,807, filed on May 31, 2007.

(52) U.S. Cl.
CPC ............ *H04R 25/60* (2013.01); *H04R 25/65* (2013.01); *H04R 25/607* (2019.05); *H04R 2225/0216* (2019.05); *H04R 2225/025* (2013.01); *H04R 2225/51* (2013.01); *H04R 2225/55* (2013.01); *H04R 2225/57* (2019.05)

(56) References Cited

U.S. PATENT DOCUMENTS

| | | |
|---|---|---|
| 3,276,028 A | 9/1966 | Mayes et al. |
| 4,334,315 A | 6/1982 | Ono et al. |
| 4,652,888 A | 3/1987 | Deasy |
| 4,741,339 A | 5/1988 | Harrison et al. |
| 4,924,237 A | 5/1990 | Honda et al. |
| 5,404,577 A | 4/1995 | Zuckerman et al. |
| 5,426,719 A | 6/1995 | Franks et al. |
| 5,434,924 A | 7/1995 | Jampolsky |
| 5,493,698 A | 2/1996 | Suzuki et al. |
| 5,621,422 A | 4/1997 | Wang |
| 5,626,630 A | 5/1997 | Markowitz et al. |
| 5,697,958 A | 12/1997 | Paul et al. |
| 5,721,783 A | 2/1998 | Anderson |
| 5,760,746 A | 6/1998 | Kawahata |
| 5,761,319 A | 6/1998 | Dar et al. |
| 5,982,764 A | 11/1999 | Palermo et al. |
| 5,991,419 A | 11/1999 | Brander |
| 6,073,050 A | 6/2000 | Griffith |
| 6,115,585 A | 9/2000 | Matero et al. |
| 6,161,036 A | 12/2000 | Matsumura et al. |
| 6,167,312 A | 12/2000 | Goedeke |
| 6,169,925 B1 | 1/2001 | Villaseca et al. |
| 6,204,819 B1 | 3/2001 | Hayes et al. |
| 6,240,317 B1 | 5/2001 | Villaseca et al. |
| 6,259,731 B1 | 7/2001 | Dent et al. |
| 6,424,820 B1 | 7/2002 | Burdick et al. |
| 6,434,429 B1 | 8/2002 | Kraus et al. |
| 6,456,720 B1 | 9/2002 | Brimhall et al. |
| 6,491,722 B1 | 12/2002 | Kroll et al. |
| 6,515,629 B1 | 2/2003 | Kuo et al. |
| 6,556,825 B1 | 4/2003 | Mansfield |
| 6,600,931 B2 | 7/2003 | Sutton et al. |
| 6,748,094 B1 | 6/2004 | Tziviskos et al. |
| 6,766,201 B2 | 7/2004 | Von Arx et al. |
| 6,786,860 B2 | 9/2004 | Maltan et al. |
| 6,839,447 B2 | 1/2005 | Nielsen et al. |
| 6,893,395 B1 | 5/2005 | Kraus et al. |
| 6,911,944 B2 | 6/2005 | Sekine et al. |
| 6,924,773 B1 | 8/2005 | Paratte |
| 7,002,521 B2 | 2/2006 | Egawa et al. |
| 7,020,298 B1 | 3/2006 | Tziviskos et al. |
| 7,027,608 B2 | 4/2006 | Fretz et al. |
| 7,031,419 B2 | 4/2006 | Piirainen |
| 7,046,499 B1 | 5/2006 | Imani et al. |
| 7,154,442 B2 | 12/2006 | Van Wonterghem et al. |
| 7,167,722 B2 | 1/2007 | Chiu et al. |
| 7,181,206 B2 | 2/2007 | Pedersen |
| 7,212,866 B1 | 5/2007 | Griffith |
| 7,256,747 B2 | 8/2007 | Victorian et al. |
| 7,277,676 B2 | 10/2007 | Sato |
| 7,446,708 B1 | 11/2008 | Nguyen et al. |
| 7,450,078 B2 | 11/2008 | Knudsen et al. |
| 7,546,149 B2 | 6/2009 | Aerrabotu et al. |
| 7,570,777 B1 | 8/2009 | Taenzer et al. |
| 7,593,538 B2 | 9/2009 | Polinske |
| 7,599,508 B1 | 10/2009 | Lynch et al. |
| 7,630,772 B1 | 12/2009 | Walsh et al. |
| 7,652,628 B2 | 1/2010 | Zweers |
| 7,689,248 B2 | 3/2010 | Valve et al. |
| 7,791,551 B2 | 9/2010 | Platz |
| 7,804,886 B2 | 9/2010 | Silver et al. |
| 7,818,029 B2 | 10/2010 | Sanguinetti |
| 7,844,242 B2 | 11/2010 | Rofougaran et al. |
| 7,864,971 B2 | 1/2011 | Kjems et al. |
| 7,925,356 B2 | 4/2011 | Li et al. |
| 7,945,064 B2 | 5/2011 | O'Brien et al. |
| 7,973,725 B2 | 7/2011 | Qi et al. |
| 7,974,716 B2 | 7/2011 | Schumaier |
| 7,978,141 B2 | 7/2011 | Chi et al. |
| 8,009,848 B2 | 8/2011 | Roeck et al. |
| 8,027,727 B2 | 9/2011 | Freeberg |
| 8,036,405 B2 | 10/2011 | Ludvigsen et al. |
| 8,041,227 B2 | 10/2011 | Holcombe et al. |
| 8,300,863 B2 | 10/2012 | Knudsen et al. |
| 8,369,959 B2 | 2/2013 | Meskens |
| 8,374,548 B2 | 2/2013 | Parkkinen et al. |
| 8,395,555 B2 | 3/2013 | Hobson et al. |
| 8,401,211 B2 | 3/2013 | Angst et al. |
| 8,422,705 B2 | 4/2013 | Kilsgaard |
| 8,433,080 B2 | 4/2013 | Rader et al. |
| 8,494,197 B2 | 7/2013 | Polinske et al. |
| 8,498,574 B2 | 7/2013 | Beninghaus et al. |
| 8,526,648 B2 | 9/2013 | Dijkstra et al. |
| 8,587,488 B2 | 11/2013 | Knudsen et al. |
| 8,594,050 B2 | 11/2013 | Kesselman |
| 8,934,984 B2 | 1/2015 | Meskens et al. |
| 8,938,305 B2 | 1/2015 | Abrahamson et al. |
| 9,114,265 B2 | 8/2015 | Mazar et al. |
| 9,446,233 B2 | 9/2016 | Meskens et al. |
| 2002/0016188 A1 | 2/2002 | Kashiwamura |
| 2002/0081987 A1 | 6/2002 | Yoshida et al. |
| 2002/0091337 A1 | 7/2002 | Adams et al. |
| 2002/0137472 A1 | 9/2002 | Quinn et al. |
| 2003/0045283 A1 | 3/2003 | Hagedoorn |
| 2003/0098812 A1 | 5/2003 | Ying et al. |
| 2004/0010181 A1 | 1/2004 | Feeley et al. |
| 2004/0013280 A1 | 1/2004 | Niederdrank |
| 2004/0037442 A1* | 2/2004 | Nielsen ............... H04R 25/552 381/315 |
| 2004/0073275 A1 | 4/2004 | Maltan et al. |
| 2004/0080457 A1 | 4/2004 | Guo et al. |
| 2004/0138723 A1* | 7/2004 | Malick ............... H04R 25/552 607/57 |
| 2004/0246179 A1 | 12/2004 | Chen et al. |
| 2005/0057426 A1 | 3/2005 | Itkin |
| 2005/0068234 A1 | 3/2005 | Hung et al. |
| 2005/0094840 A1 | 5/2005 | Harano |
| 2005/0099341 A1 | 5/2005 | Zhang et al. |
| 2005/0100185 A1 | 5/2005 | Connors et al. |
| 2005/0244024 A1 | 11/2005 | Fischer et al. |
| 2005/0245289 A1 | 11/2005 | Yoshino |
| 2005/0248717 A1 | 11/2005 | Howell et al. |
| 2005/0251225 A1 | 11/2005 | Faltys et al. |
| 2006/0012524 A1 | 1/2006 | Mierke et al. |
| 2006/0018496 A1 | 1/2006 | Niederdrank et al. |
| 2006/0039577 A1 | 2/2006 | Sanguino et al. |
| 2006/0046719 A1 | 3/2006 | Holtschneider |
| 2006/0052144 A1 | 3/2006 | Seil et al. |
| 2006/0056649 A1 | 3/2006 | Schumaier |
| 2006/0061512 A1 | 3/2006 | Asano et al. |
| 2006/0064037 A1 | 3/2006 | Shalon et al. |
| 2006/0071869 A1 | 4/2006 | Yoshino et al. |
| 2006/0111044 A1 | 5/2006 | Keller |
| 2006/0115103 A1 | 6/2006 | Feng et al. |

(56) References Cited

U.S. PATENT DOCUMENTS

| | | |
|---|---|---|
| 2006/0177081 A1 | 8/2006 | Bauml et al. |
| 2006/0181466 A1 | 8/2006 | Krupa |
| 2006/0192723 A1 | 8/2006 | Harada et al. |
| 2006/0221902 A1 | 10/2006 | Chen et al. |
| 2007/0036280 A1* | 2/2007 | Roeck .......... H04R 25/558 379/52 |
| 2007/0080889 A1 | 4/2007 | Zhang |
| 2007/0123174 A1 | 5/2007 | Wiessner et al. |
| 2007/0171134 A1 | 7/2007 | Yoshino et al. |
| 2007/0218846 A1 | 9/2007 | Neill et al. |
| 2007/0229369 A1 | 10/2007 | Platz |
| 2007/0229376 A1 | 10/2007 | Desclos et al. |
| 2007/0230714 A1* | 10/2007 | Armstrong .......... H04R 25/552 381/74 |
| 2007/0230727 A1 | 10/2007 | Sanguino et al. |
| 2007/0285321 A1 | 12/2007 | Chung et al. |
| 2008/0024375 A1 | 1/2008 | Martin et al. |
| 2008/0032636 A1 | 2/2008 | Coombs |
| 2008/0056520 A1 | 3/2008 | Christensen et al. |
| 2008/0079645 A1 | 4/2008 | Higasa et al. |
| 2008/0123866 A1 | 5/2008 | Rule et al. |
| 2008/0158068 A1 | 7/2008 | Huang et al. |
| 2008/0165994 A1 | 7/2008 | Caren et al. |
| 2008/0177353 A1 | 7/2008 | Hirota et al. |
| 2008/0231524 A1 | 9/2008 | Zeiger et al. |
| 2008/0300658 A1 | 12/2008 | Meskens |
| 2008/0304686 A1 | 12/2008 | Meskens et al. |
| 2008/0320587 A1 | 12/2008 | Vauclair et al. |
| 2009/0030484 A1 | 1/2009 | Chambers |
| 2009/0069060 A1 | 3/2009 | Kim |
| 2009/0074221 A1 | 3/2009 | Westermann |
| 2009/0124201 A1 | 5/2009 | Meskens |
| 2009/0169038 A1 | 7/2009 | Knudsen et al. |
| 2009/0196444 A1 | 8/2009 | Solum |
| 2009/0214064 A1 | 8/2009 | Wu et al. |
| 2009/0231204 A1 | 9/2009 | Shaker et al. |
| 2009/0231211 A1 | 9/2009 | Zweers |
| 2009/0243944 A1 | 10/2009 | Jung et al. |
| 2009/0273530 A1 | 11/2009 | Chi et al. |
| 2009/0315787 A1 | 12/2009 | Schatzle |
| 2010/0020994 A1 | 1/2010 | Christensen et al. |
| 2010/0033380 A1 | 2/2010 | Pascolini et al. |
| 2010/0079287 A1 | 4/2010 | Forster et al. |
| 2010/0097275 A1 | 4/2010 | Parsche et al. |
| 2010/0109953 A1 | 5/2010 | Tang |
| 2010/0158291 A1 | 6/2010 | Polinske et al. |
| 2010/0158293 A1 | 6/2010 | Polinske et al. |
| 2010/0158295 A1 | 6/2010 | Polinske et al. |
| 2010/0172525 A1 | 7/2010 | Angst et al. |
| 2010/0195836 A1 | 8/2010 | Platz |
| 2010/0245201 A1 | 9/2010 | Hossain et al. |
| 2010/0285851 A1 | 11/2010 | Horihata et al. |
| 2010/0321269 A1 | 12/2010 | Ishibana et al. |
| 2011/0007927 A1 | 1/2011 | Hedrick et al. |
| 2011/0022121 A1 | 1/2011 | Meskins |
| 2011/0129094 A1 | 6/2011 | Petersen |
| 2011/0249836 A1 | 10/2011 | Solum et al. |
| 2011/0285599 A1 | 11/2011 | Smith |
| 2011/0294537 A1 | 12/2011 | Vance |
| 2012/0087506 A1 | 4/2012 | Ozden |
| 2012/0093324 A1 | 4/2012 | Sinasi |
| 2012/0154222 A1 | 6/2012 | Oh et al. |
| 2012/0326938 A1 | 12/2012 | Grossman et al. |
| 2013/0308805 A1 | 11/2013 | Ozden |
| 2013/0342407 A1 | 12/2013 | Kvist et al. |
| 2014/0010392 A1 | 1/2014 | Kvist |
| 2014/0097993 A1 | 4/2014 | Hotta et al. |
| 2014/0185848 A1 | 7/2014 | Ozden et al. |
| 2014/0321685 A1 | 10/2014 | Rabel |
| 2014/0378958 A1 | 12/2014 | Leussler |
| 2015/0289067 A1 | 10/2015 | Riepenhoff |
| 2016/0330552 A1 | 11/2016 | Flood |
| 2018/0376235 A1 | 12/2018 | Leabman et al. |

FOREIGN PATENT DOCUMENTS

| | | |
|---|---|---|
| CN | 102318138 A | 1/2012 |
| CN | 102570000 A | 7/2012 |
| DE | 3625891 A1 | 2/1988 |
| DE | 10 2004 017832 | 10/2005 |
| DE | 10 2008 022 127 A1 | 11/2009 |
| EP | 1231 819 A2 | 8/2002 |
| EP | 1294 049 A1 | 3/2003 |
| EP | 1414271 A2 | 4/2004 |
| EP | 1 465 457 A2 | 10/2004 |
| EP | 1 465 457 A3 | 10/2004 |
| EP | 1 589 609 | 10/2005 |
| EP | 1 594 188 A1 | 11/2005 |
| EP | 1 681 903 A2 | 7/2006 |
| EP | 1720375 A1 | 11/2006 |
| EP | 1 763 145 A1 | 3/2007 |
| EP | 1939 984 A1 | 2/2008 |
| EP | 1 953 934 A1 | 8/2008 |
| EP | 2076065 A1 | 1/2009 |
| EP | 2088804 A1 | 8/2009 |
| EP | 2 200 120 A2 | 6/2010 |
| EP | 2 200 120 A3 | 6/2010 |
| EP | 2 207 238 A1 | 7/2010 |
| EP | 2 229 009 A1 | 9/2010 |
| EP | 2227042 A1 | 9/2010 |
| EP | 2 302 737 | 3/2011 |
| EP | 2 458 674 A2 | 5/2012 |
| EP | 2 637 251 | 11/2013 |
| EP | 2 680 366 | 1/2014 |
| EP | 2 723 101 A2 | 4/2014 |
| EP | 2 723 101 A3 | 4/2014 |
| EP | 2 765 650 | 8/2014 |
| JP | S59-97204 | 6/1984 |
| JP | HI 0-209739 | 8/1998 |
| JP | 2005-304038 A | 10/2005 |
| JP | 2006025392 | 1/2006 |
| JP | 2006-033853 A | 2/2006 |
| JP | 2007013247 A | 1/2007 |
| JP | 2012-090266 | 5/2012 |
| KR | 10-0804843 B1 | 2/2008 |
| WO | 98/44762 | 10/1998 |
| WO | 98/52295 A1 | 11/1998 |
| WO | 01/47126 A2 | 6/2001 |
| WO | 2002074011 A2 | 9/2002 |
| WO | 03/026342 | 3/2003 |
| WO | 03/094346 A1 | 11/2003 |
| WO | 03/107548 | 12/2003 |
| WO | 2004/110099 A1 | 12/2004 |
| WO | 2005/076407 A2 | 8/2005 |
| WO | 2005/081583 A1 | 9/2005 |
| WO | 2006/055884 A2 | 5/2006 |
| WO | 200612283 A2 | 11/2006 |
| WO | 2007/045254 A1 | 4/2007 |
| WO | 2007/140403 A2 | 6/2007 |
| WO | 2008/012355 A1 | 1/2008 |
| WO | 200892183 A1 | 8/2008 |
| WO | 2009/010724 A1 | 1/2009 |
| WO | 2009/098858 A1 | 8/2009 |
| WO | 2009117778 A1 | 10/2009 |
| WO | 2010/065356 A1 | 6/2010 |
| WO | 2011099226 | 8/2011 |
| WO | 2012059302 | 5/2012 |
| WO | 2014090420 A1 | 6/2014 |

OTHER PUBLICATIONS

Advisory Action dated Aug. 29, 2014 for U.S. Appl. No. 13/740,471.

Chinese Office Action and Search Report dated Dec. 4, 2013 for related CN Patent Application No. 201110317229.4.

Chinese Office Action and Search Report dated Nov. 12, 2013 for related CN Patent Application No. 201110317264.6.

Danish Office Action dated Apr. 30, 2012 for Danish Patent Application No. PA 2011 70566.

Danish Office Action dated May 1, 2012 for Danish Patent Application No. PA 2011 70567.

English Abstract of Foreign Reference DE 10 2008 022 127 AI.

(56) References Cited

OTHER PUBLICATIONS

Extended European Search Report dated Apr. 17, 2014 for EP Patent Application No. 13192316.1.
Extended European Search Report dated Apr. 22, 2014 for EP Patent Application No. 13192323. 7.
Extended European Search Report dated Mar. 7, 2014 for EP Patent Application No. 11184503.8.
Extended European Search Report dated Mar. 7, 2014 for EP Patent Application No. 11184507.9.
Extended European Search Report dated May 6, 2014 for EP Patent Application No. 13175258.6.
Final Office Action dated Aug. 29, 2014 for U.S. Appl. No. 13/848,605.
Final Office Action dated Feb. 27, 2014, for U.S. Appl. No. 13/271,180.
Final Office Action dated May 19, 2014 for U.S. Appl. No. 13/740,471.
First Danish Office Action dated Apr. 26, 2011 for Danish Patent Application No. PA 2010 00931.
First Office Action dated Feb. 12, 2013 for Japanese Patent Application No. 2011-224711.
First Technical Examination and Search Report Dated Jan. 18, 2013 for DK Patent Application No. PA 2012 70410, 4 pages.
Fourth Danish Office Action, Intention to Grant dated Feb. 13, 2013 for Danish Patent Application No. PA 2010 00931.
Non-final Office Action dated Jan. 2, 2014 for U.S. Appl. No. 13/740,471.
Non-Final Office Action dated Jul. 29, 2014 for U.S. Appl. No. 13/917,448.
Non-Final Office Action dated Mar. 27, 2014 for U.S. Appl. No. 13/848,605.
Non-Final Office Action dated May 22, 2014 for U.S. Appl. No. 13/271,170.
Non-final Office Action dated Oct. 8, 2013 for U.S. Appl. No. 13/271,180.
Notice of Reasons for Rejection dated May 21, 2013 for Japanese Patent Application No. 2011-224705.
Second Danish Office Action dated Apr. 24, 2012 for Danish Patent Application No. PA 2010 00931.
Second Technical Examination—Intention to Grant dated Jul. 8, 2013 for DK Patent Application No. PA 2012 70412, 2 pages.
Second Technical Examination dated Aug. 6, 2013 for DK Patent Application No. PA 2012 70411, 2 pages.
Second Technical Examination dated Jul. 12, 2013, for DK Patent Application No. PA 2012 70410, 2 pages.
Third Technical Examination dated Jan. 31, 2014, for DK Patent Application No. PA 2012 70410, 2 pages.
Office Action dated Jun. 17, 2014 in Japanese Patent Application No. 2013- 258396, 3 pages.
First Technical Examination dated Jun. 25, 2014 for DK Patent Application No. PA 2013 70665, 5 pages.
First Technical Examination dated Jun. 26, 2014 for DK Patent Application No. PA 2013 70664, 5 pages.
Extended European Search Report dated May 14, 2014 for EP Patent Application No. 13192322.9.
First Technical Examination and Search Report dated Jun. 27, 2014 for DK Patent Application No. PA 2013 70666.
Non-final Office Action dated Nov. 18, 2014 for U.S. Appl. No. 13/271,180.
Conway et al., Antennas for Over-Body-Surface Communication at 2.45 GHz, Apr. 2009, IEEE Transactions on Antennas and Propagation, vol. 57, No. 4, pp. 844-855.
Non-final Office Action dated Nov. 19, 2014 for U.S. Appl. No. 13/931,556.
Non-final Office Action dated Dec. 18, 2014 for U.S. Appl. No. 13/740,471.
Final Office Action dated Dec. 31, 2014 for U.S. Appl. No. 13/271,170.
Non-final Office Action dated Jan. 5, 2015 for U.S. Appl. No. 13/848,605.
Extended European Search Report dated Oct. 9, 2014 for EP Patent Application No. 14181165.3.
"Novelty Search including a Preliminary Patentability Opinion Report", in reference to P81007295DK02, dated Jul. 28, 2011 (8 pages).
"Novelty Search including a Preliminary Patentability Opinion Report", in reference to P81I 01358DK01, dated Jul. 28, 2011 (8 pages).
Non-final Office Action dated Jan. 15, 2015 for U.S. Appl. No. 14/199,511.
Non-final Office Action dated Feb. 5, 2015 for U.S. Appl. No. 14/198,396.
Non-final Office Action dated Feb. 24, 2015 for U.S. Appl. No. 14/202,486.
Notice of Allowance dated Mar. 5, 2015 for U.S. Appl. No. 13/917,448.
Notice of Allowance dated Apr. 24, 2015 for U.S. Appl. No. 13/931,556.
First Technical Examination and Search Report dated Mar. 9, 2015, for related Danish Patent Application No. PA 2014 70489.
Non-final Office Action dated May 7, 2015 for U.S. Appl. No. 13/271,180.
Advisory Action dated May 14, 2015 for U.S. Appl. No. 13/271,170.
Notice of Allowance and Fee(s) Due dated May 22, 2015 for U.S. Appl. No. 13/848,605.
Non-final Office Action dated Jun. 10, 2015 for U.S. Appl. No. 14/199,263.
Notice of Allowance and Fee(s) Due dated Jun. 18, 2015, for U.S. Appl. No. 13/917,448.
Communication pursuant to Article 94(3) EPC dated Mar. 16, 2015, for related European Patent Application No. 11 184 503.8, 12 pages.
Communication pursuant to Article 94(3) EPC dated Mar. 19, 2015, for related European Patent Application No. 11 184 507.9, 12 pages.
Non-final Office Action dated Jul. 1, 2015 for U.S. Appl. No. 14/199,070.
Final Office Action dated Jul. 15, 2015 for related U.S. Appl. No. 13/740,471.
Notice of Allowance and Fees Due dated Aug. 3, 2015 for related U.S. Appl. No. 13/931,556.
Non-final Office Action dated Aug. 17, 2015 for related U.S. Appl. No. 14/198,396.
Non-final Office Action dated Aug. 25, 2015 for related U.S. Appl. No. 14/202,486.
Notice of Allowance and Fee(s) Due dated Sep. 2, 2015 for related U.S. Appl. No. 14/199,511.
Notice of Allowance and Fee(s) Due dated Sep. 3, 2015 for related U.S. Appl. No. 13/848,605.
Notice of Allowance and Fee(s) Due dated Sep. 25, 2015 for related U.S. Appl. No. 13/271,170.
Notice of Allowance and Fee(s) Due dated Nov. 18, 2015 for related U.S. Appl. No. 13/931,556.
Final Office Action dated Nov. 18, 2015 for related U.S. Appl. No. 14/199,263.
Non-final Office Action dated Dec. 2, 2015 for related U.S. Appl. No. 13/271,180.
Notice of Allowance and Fee(s) Due dated Dec. 18, 2015 for related U.S. Appl. No. 13/917,448.
Notification of Reasons for Rejection dated Nov. 24, 2015 for related Japanese Patent Application No. 2014-228343, 8 pages.
Notice of Allowance and Fee(s) Due dated Feb. 16, 2016 for related U.S. Appl. No. 13/740,471.
Advisory Action dated Feb. 1, 2016 for related U.S. Appl. No. 14/199,263.
Notice of Allowance and Fees Due dated Mar. 3, 2016 for related U.S. Appl. No. 13/931,556.
Final Office Action dated Mar. 22, 2016 for related U.S. Appl. No. 14/202,486.
Notice of Allowance and Fee(s) due dated Mar. 23, 2016 for related U.S. Appl. No. 14/198,396.
Final Office Action dated Apr. 4, 2016 for related U.S. Appl. No. 13/271,180.
Final Office Action dated Apr. 15, 2016 for related U.S. Appl. No. 14/199,070.

(56) References Cited

OTHER PUBLICATIONS

Notice of Allowance and Fee(s) dated May 25, 2016 for related U.S. Appl. No. 14/199,263.
Notice of Allowance and Fee(s) dated Jun. 17, 2016 for related U.S. Appl. No. 13/917,448.
Non-final Office Action dated Sep. 15, 2011 for related U.S. Appl. No. 12/131,867.
Non-final Office Action dated Feb. 10, 2012 for related U.S. Appl. No. 12/131,867.
Final Office Action dated Aug. 23, 2012 for related U.S. Appl. No. 12/131,867.
Non-Final Office Action dated Mar. 7, 2014 for related U.S. Appl. No. 12/131,867.
Notice of Allowance and Fee(s) due dated Sep. 12, 2014 for related U.S. Appl. No. 12/131,867.
Petition for Inter Partes Review, Inter Parties Review No. IPR2015-00104, Paper 1 (PTAB Oct. 21, 2014).
Declaration of Professor Bruce McNair, Inter Parties Review No. IPR2015-00104, Exhibit 1012 (PTAB Oct. 21, 2014).
Decision, Institution of Inter Partes Review, Inter Parties Review No. IPR2015-00104, Paper 8 (PTAB Apr. 29, 2015).
Petitioner's Reply to Patent Owner's Response, Inter Parties Review No. IPR2015-00104, Paper 16 (PTAB Oct. 29, 2015).
Order, Joint Motion to Terminate, Inter Parties Review No. IPR2015-00104, Paper 24 (PTAB Jan. 12, 2016).
Petition for Inter Partes Review, Inter Parties Review No. IPR2015-00103, Paper 1 (PTAB Oct. 21, 2014).
Declaration of Professor Bruce McNair, Inter Parties Review No. IPR2015-00103, Exhibit 1012 (PTAB Feb. 9, 2015).
Decision, Institution of Inter Partes Review, Inter Parties Review No. IPR2015-00103, Paper 10 (PTAB Apr. 29, 2015).
Petitioner's Request for Rehearing, Inter Parties Review No. IPR2015-00103, Paper 12 (PTAB May 8, 2015).
Decision, Petitioner's Request for Rehearing, Inter Parties Review No. IPR2015-00103, Paper 13 (PTAB Jun. 18, 2015).
Judgment, Request for Adverse Judgment, , Inter Parties Review No. IPR2015-00103, Paper 19 (PTAB Oct. 7, 2015).
Complaint, Oticon v. GN Hearing, Case No. 0:17-cv-00499, United States District Court, District of Minnesota (Feb. 17, 2017).
Notice of Dismissal, Oticon v. GN Hearing, Case No. 0:17-cv-00499, United States District Court, District of Minnesota (Dec. 4, 2017).
Final Office Action dated Oct. 2, 2018 for related U.S. Appl. No. 15/641,133.
Final Office Action dated Sep. 26, 2018 for related U.S. Appl. No. 14/461,983.
Office action dated Jul. 3, 2018 for corresponding Japanese patent application No. 2015 159910.
Non-final Office Action dated Jan. 31, 2018 for related U.S. Appl. No. 15/641,133.
Non-final Office Action dated Feb. 23, 2018 for related U.S. Appl. No. 14/461,983.
Communication pursuant to Article 94(3) EPC dated Jan. 30, 2018, for related European Patent Application No. 14 181165.3, 8 pages.
Notice of Allowance and Fee(s) due dated Nov. 22, 2017 for related U.S. Appl. No. 15/455,081.
Final Office Action dated Sep. 8, 2017 for related U.S. Appl. No. 15/455,081.
Advisory Action dated Sep. 5, 2017 for related U.S. Appl. No. 14/461,983.
Notice of Allowance and Fee(s) dated Sep. 27, 2017 for related U.S. Appl. No. 14/199,070.
First Amended Complaint filed Jun. 12, 2017 in the U.S. District Court, District of Minnesota, for Case No. 17-499, 26 pages.
Exhibit 3 of the First Amended Compliant for Non Patent Literature Document No. 1, cited herewith, dated Jun. 12, 2017, 65 pages.
Exhibit 4 of the First Amended Compliant for Non Patent Literature Document No. 1, cited herewith, dated Jun. 12, 2017, 60 pages.
Exhibit 8 of the First Amended Compliant for Non Patent Literature Document No. 1, cited herewith, dated Jun. 12, 2017, 55 pages.
Exhibit 9 of the First Amended Compliant for Non Patent Literature Document No. 1, cited herewith, dated Jun. 12, 2017, 56 pages.
Final Office Action dated May 19, 2017 for related U.S. Appl. No. 14/461,983.
Final Office Action dated Jun. 21, 2017 for related U.S. Appl. No. 14/199,070.
Notification of First Office Action dated Feb. 21, 2017 for related Chinese Patent Application No. 201410641926.9, 16 pages.
Notification of First Office Action dated Jan. 16, 2017 for related Chinese Patent Application No. 201410643821.7, 14 pages.
Non-final Office Action dated May 12, 2017 for related U.S. Appl. No. 15/455,081.
Notice of Allowance and Fee(s) due dated Apr. 11, 2017 for related U.S. Appl. No. 13/271,180.
Notification of First Office Action dated Jan. 26, 2017 for related Chinese Patent Application No. 201310713296.7, 21 pages.
Notice of Allowance and Fee(s) Due dated Feb. 16, 2017 for related U.S. Appl. No. 14/202,486.
Complaint dated Feb. 17, 2017 for U.S. District Court, District of Minnesota, Case No. 17-499, 14 pages.
Transcript of Bruce McNair for IPR2015-00103, IPR2015-00104, Jul. 21, 2015, 90 pages.
Declaration of professor Bruce McNair for IPR against U.S. Pat. No. 8,300,863, Sep. 9, 2014, 54 pages.
File History for Inter-Parte-Review No. IPR2015-01947, 678 pages.
File History for Inter-Parte-Review No. IPR2015-01948, 663 pages.
European Communication pursuant to Article 94(3) EPC dated Dec. 20, 2016 for related EP Patent Application No. 13192323.7, 4 pages.
"The 1987 ARRL Handbook for the Radio Amateur," Published by: The American Radio Relay League, 1986, Sixty-Fourth Edition, 10 pages.
IEEE 100, "The Authoritative Dictionary of IEEE Standards Terms," Seventh Edition, Dec. 2000, 3 pages.
H. Newton, "Newton's Telecom Dictionary," Twenty-second Edition, Feb. 2006, 3 pages.
IEEE 100, "The Authoritative Dictionary of IEEE Standards Terms," Seventh Edition, 2000, 12 pages.
K Fujimoto, et al., "Small Antennas," Research Studies Press, Feb. 1987, 11 pages.
Carl E. Smith, et al., "Performance of Short Antennas" Proceedings of the I.RE., Oct. 1947, 13 pages.
Kurt Ikrath, et al., "Performance of Trees as Radio Antennas in Tropical Jungle Resorts", Feb. 1972, 66 pages.
"The 1987 ARRL Handbook for the Radio Amateur," Published by: The American Radio Relay League, Newington, CT 06111, USA, 1986, Sixty-Fourth Edition, 5 pages.
U.S. Appl. No. 60/924,800, filed May 31, 2007, 62 pages.
Prosecution History of U.S. Pat. No. 8,300,863 (U.S. Appl. No. 12/342,241).
Prosecution History of U.S. Appl. No. 90/013,189, filed Mar. 25, 2014.
Prosecution History of U.S. Appl. No. 90/013,592, filed Sep. 22, 2015.
File History for Inter-Parte-Review No. IPR 2015-00104.
File History for Inter-Parte-Review No. IPR 2015-00103.
Non-final Office Action dated Sep. 29, 2016 for related U.S. Appl. No. 14/461,983.
Notice of Allowance and Fee(s) due dated Oct. 5, 2016 for related U.S. Appl. No. 13/271,180.
Non-final Office Action dated Oct. 24, 2016 for related U.S. Appl. No. 14/199,070.
Notice of Allowance and Fee(s) due dated Oct. 25, 2016 for related U.S. Appl. No. 14/202,486.
Advisory Action dated Jul. 26, 2016 for related U.S. Appl. No. 13/271,180.
1st Technical Examination and Search Report dated Jan. 24, 2013 for DK Patent Application No. PA 2012 70411, 5 pages.

* cited by examiner

ACOUSTIC OUTPUT DEVICE WITH ANTENNA

CROSS-REFERENCE TO RELATED APPLICATION

This application is a divisional of U.S. patent application Ser. No. 17/844,960, filed Jun. 21, 2022, which is a continuation of U.S. patent application Ser. No. 17/565,676, filed Dec. 30, 2021, now U.S. Pat. No. 11,491,331, which is a continuation of U.S. patent application Ser. No. 17/405,287, filed Aug. 8, 2018, which is a continuation of U.S. patent application Ser. No. 16/274,363, filed Feb. 13, 2019, now U.S. Pat. No. 11,123,559, which is a continuation of U.S. patent application Ser. No. 15/188,780, filed Jun. 21, 2016, now U.S. Pat. No. 10,219,084, which is a continuation of U.S. patent application Ser. No. 14/199,263, filed Mar. 6, 2014, now U.S. Pat. No. 9,446,233, which is a continuation of U.S. patent application Ser. No. 12/131,867, filed Jun. 2, 2008, now U.S. Pat. No. 8,934,984, which claims priority from U.S. Provisional Patent Application No. 60/924,800, filed on May 31, 2007, and U.S. Provisional Application No. 60/924,807, filed on May 31, 2007. All of the above-mentioned applications are hereby expressly incorporated by reference herein.

BACKGROUND

Field of the Invention

The present invention relates generally to hearing devices.

Related Art

Hearing aid prostheses, such as those designed to be worn behind the ear of the recipient, commonly referred to as behind-the-ear (BTE) devices, may be components of conventional hearing aids, cochlear implants, and/or the like. BTE devices, whether implemented as a component of a hearing aid, cochlear implant, middle ear implant or other hearing prosthesis, are collectively and generally referred to herein as a BTE prosthetic devices.

Conventional hearing aids may include external sound processors which input the processed (and amplified) sound in the ear by an external, or in-the ear speaker. Cochlear implants have been developed to assist people who are profoundly deaf or severely hearing impaired, by enabling them to experience a hearing sensation representative of the natural hearing sensation. In most such cases, these individuals have an absence of or destruction of the hair cells in the cochlea which naturally transduce acoustic signals into nerve impulses which are interpreted by the brain as sound. The cochlear implant therefore bypasses the hair cells to directly deliver electrical stimulation to the auditory nerves with this electrical stimulation being representative of the sound.

Cochlear implants have traditionally comprised two parts, an external component and an implanted receiver/stimulator unit. The external component can be been worn on the body of a recipient, classically as a BTE prosthetic device. The purpose of such a BTE prosthetic device has been to detect external sound using a microphone and convert the detected sound into a coded signal through an appropriate speech processing strategy.

This coded signal is then sent via a transcutaneous link to receiver/stimulator unit which is implanted in the mastoid bone of the recipient. A transcutaneous link is a magnetic induction link between a coil antenna of the implant and an externally applied coil antenna. The receiver/stimulator unit processes the coded signal into a series of stimulation sequences which are then applied directly to the auditory nerve via a series of electrodes positioned within the cochlea proximal to the modiolus of the cochlea.

The externally applied coil antenna typically forms part of a headpiece, which is applied in close proximity of the coil antenna of the implant and is connected to an external speech processor, such as a device for behind the ear. The magnetic induction link (established in a reactive near-field) typically allows bidirectional communication and power transfer towards the implant.

SUMMARY

In accordance with aspects of the present invention, a behind-the-ear (BTE) prosthetic device for use in a medical system is provided. The BTE prosthetic device comprises: a connector configured to mechanically attach an auxiliary device to the BTE prosthetic device; and a transceiver comprising one or more of an RF transmitter and an RF receiver, wherein the connector is electrically connected to the RF transceiver, and wherein the connector operates as an electromagnetic antenna for wireless communication between the BTE prosthetic device and one or more other components of the system.

In accordance with other aspects of the present invention, a cochlear implant system is provided. The cochlear implant system comprises: an implantable component; an external auxiliary component; and a behind-the-ear (BTE) prosthetic device comprising: a connector configured to mechanically attach said auxiliary device to said BTE prosthetic device; and an transceiver comprising one or more of an RF transmitter and an RF receiver, wherein said connector is electrically connected to said transceiver, and wherein said connector is configured to operate as an electromagnetic antenna for wireless communication between said BTE prosthetic device and said implantable component.

In accordance with other aspects of the present invention, a hearing device is provided. The hearing device comprises a first portion configured to be arranged at a head of a user and to provide a signal to a second portion; the second portion configured to be arranged in an ear or an ear canal of the user and to provide acoustic output to the user, the second portion including a transducer for converting the signal into the acoustic output; an antenna for wireless communication, the antenna comprising an electrically conducting element; and a coupling element coupling the first portion and the second portion, the coupling element comprising the electrically conducting element.

In accordance with other aspects of the present invention, a hearing device is provided. The hearing device comprises a first portion configured to be arranged at a head of a user and to provide a signal to a second portion; the second portion configured to be arranged in an ear or an ear canal of the user and to provide acoustic output to the user, the second portion including a transducer for converting the signal into the acoustic output; a coupling element coupling the first portion and the second portion, the coupling element configured to transmit the signal from the first portion to the second portion, the coupling element including an electrically conducting element; wherein the electrically conducting element in the coupling element is configured to operate as a part of an antenna for wireless communication.

In accordance with one embodiment of the present invention, an active implantable medical device is disclosed, comprising: an antenna and a band diplexer connected to the antenna, wherein the band diplexer comprises first filter means for a first signal to be transmitted and/or received in a first RF band and second filter means for a second signal to be transmitted and/or received in a second RF band, the second RF band being higher in frequency than the first RF band.

BRIEF DESCRIPTION OF THE DRAWINGS

Illustrative embodiments of the present invention are described herein with reference to the accompanying drawings, in which.

DETAILED DESCRIPTION

Aspects of the present invention are generally directed to a connector for a prosthesis configured to be worn behind the ear of an individual or recipient, commonly referred to as behind-the-ear (BTE) devices. BTE devices may be a component of a conventional hearing aid and/or cochlear implant, or a component of any other medical systems or prosthesis. BTE devices, whether implemented as a component of a hearing aid, cochlear implant, middle ear implant or other medical systems/prosthesis, are collectively and generally referred to herein as a BTE prosthetic devices.

In certain aspects of the present invention, a BTE prosthetic device for use in a medical system or prosthesis, (collectively and generally referred to as medical systems herein) comprises a connector configured to mechanically attach an auxiliary device of the system to the BTE prosthetic device. The connector is electrically connected to a transceiver of the BTE prosthetic device. The transceiver may comprise any combination of a transmitter and/or a receiver. Furthermore, the transceiver may comprise only a transmitter or a receiver. The connector is configured to operate as an electromagnetic antenna for transmitting and/or receiving signals between the BTE prosthetic and other components of the medical system. The electromagnetic antenna may be, for example, operable in the far-field.

Figure 1:
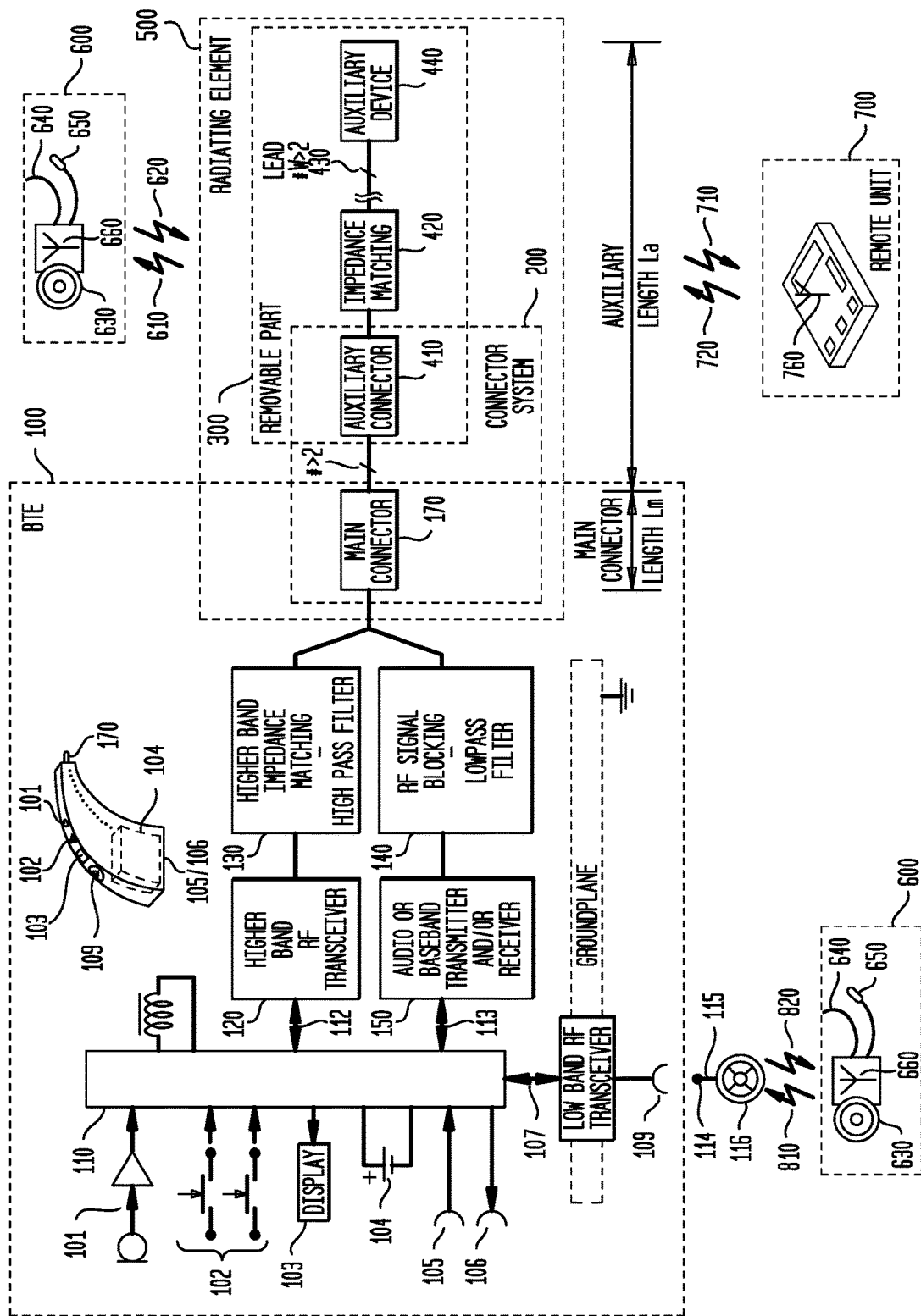
FIG. 1 is a schematic block diagram of a behind-the-ear (BTE) prosthetic device having an integrated antenna and connector in accordance with embodiments of the present invention.

As noted, embodiments of the present invention may be implemented with a number of BTE prosthetic devices in a variety of medical systems. Embodiments of the present invention will be described herein with reference to one specific type of BTE prosthetic device and medical system, namely a BTE prosthetic device which is a component of a partially implantable hearing aid system. FIG. 1 illustrates such a partially implantable hearing aid system, comprising BTE prosthetic device 100 in communication with one or more cochlear stimulating implants, shown generally as implants 600 and one or more remote units 700. Implants 600 may each comprise a variety of implantable cochlear stimulating devices, such as an implantable electrode arrays, middle ear implants, or the like. As described in more detail below, BTE prosthetic device 100 may communicate with other components of the partially implantable hearing aid system via one or more wireless communication links, shown as communication links 610, 620, 710, 720, 810 and 820.

In the illustrated embodiment of FIG. 1, BTE prosthetic device 100 comprises a microphone 101 to receive acoustic sounds, and a signal processor 110. BTE prosthetic device 100 converts and processes the received acoustic sounds received by microphone 101, or various other received auditory signals, to a format which may be used by the implants 600. In accordance with the illustrated embodiments, BTE prosthetic device 100 further comprises one or more transceivers 108 which may transmit processed signals to implants 600.

BTE prosthetic device 100 has sufficient persistent and non-persistent memory. Furthermore, BTE prosthetic device 100 is powered by a battery 104. Additional controls 102 and interfaces 103 facilitate human interaction with the hearing aid system. In certain embodiments, the main housing of BTE prosthetic device 100 may accept removable plug-in modules, such as batteries, an ear hook, a headpiece, etc. BTE prosthetic device 100 may also be provided with input and output jacks 105 and 106.

As noted, a variety of cochlear stimulating implants may be used in accordance with embodiments of the present invention. FIG. 1 illustrates specific implants 600 which comprise an implantable electrode array 640 that stimulate the recipient's cochlea with electrical signals. The implant converts the signals received from the BTE prosthetic device 100 into stimuli signals and then applies them to the cochlea via electrode array 640. Depending on cause of the recipient's deafness, implant 600 may optionally comprise a mechanical implantable actuator 650 configured to stimulate middle or inner ear parts, in addition to, or in place of, electrode array 640.

In embodiments of the present invention, BTE prosthetic device 100 comprises a lower radio frequency (RF) band transceiver 108 for wireless communication over a magnetic induction link, such as links 810 and 820. Transceiver 108 may be configured to transmit and/or receive wireless communications. Low RF band transceiver 108 may be connected, in certain embodiments, to a connector socket 109, which accepts a plug 114 of a headpiece 116. Headpiece 116 comprises an extension cable 115 between plug 114 and an antenna coil or closed-wire loop 116. Antenna coil 116 is configured to transmit signals to coil antenna 630 of an implant 600, and/or receive signals from coil antenna 630. Antennas 116 and 630 may be placed in close proximity of each other.

The above-described communication link 810 and 820 between BTE prosthetic device 100 and implant 600 operates in the reactive near-field, by magnetic induction in a non-propagating quasi-static magnetic field. Both bidirectional data transfer and power transfer towards the implant are possible.

In accordance with certain embodiments of the present invention, communication between components of a medical system may occur in a near-field or far EM-field, via, for example, electromagnetic field propagation. This type of communication has the advantage that it takes place over larger distances, which would permit components of the communication link to be spaced apart by larger distances than permitted in a conventional RF link. Furthermore, wireless communication between the BTE prosthetic device 100 and other external devices 700 may also preferably take place in the propagating far-field. An antenna tuned to the frequency range of operation is generally used for efficient communication using the EM-field. Whereas a magnetic induction link uses a coil or closed-wire antenna, transmission and reception by electromagnetic field propagation may be carried out with open-ended antennas.

Figure 2A:
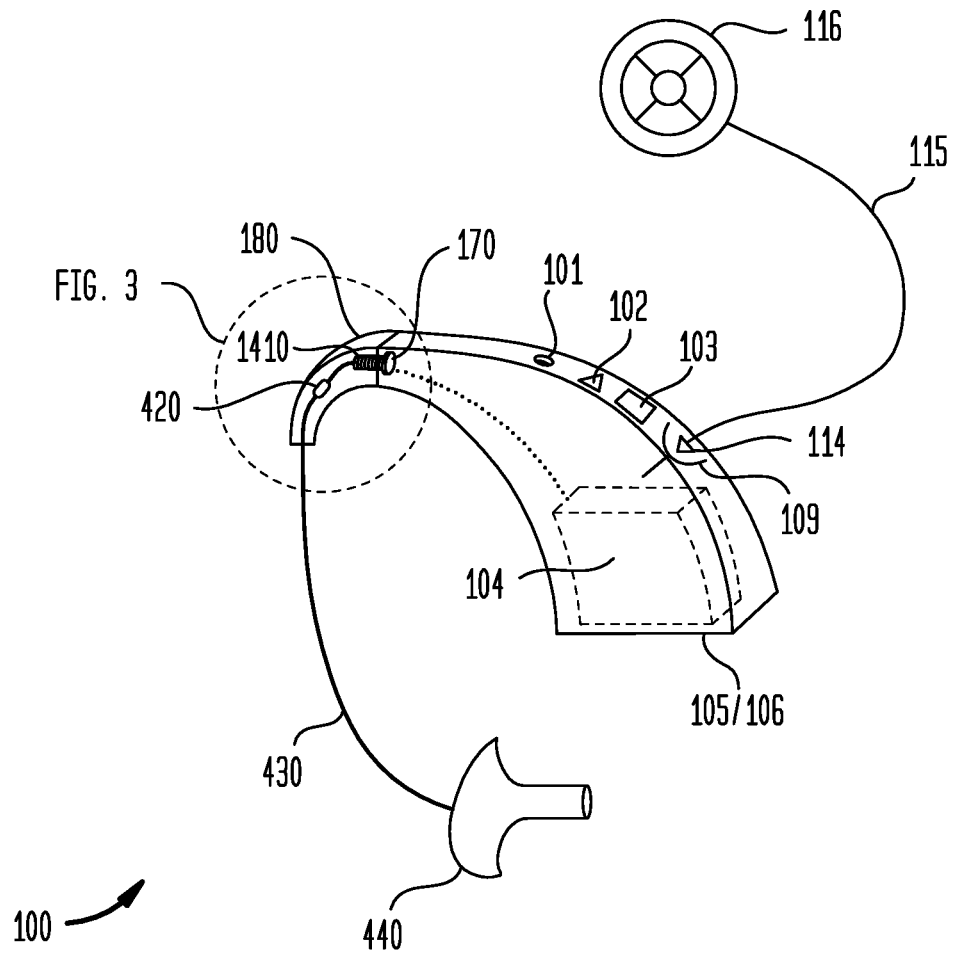
FIG. 2A illustrates a BTE prosthetic device having an ear hook and auxiliary device with extension antenna in accordance with embodiments of the present invention.
Figure 2B:
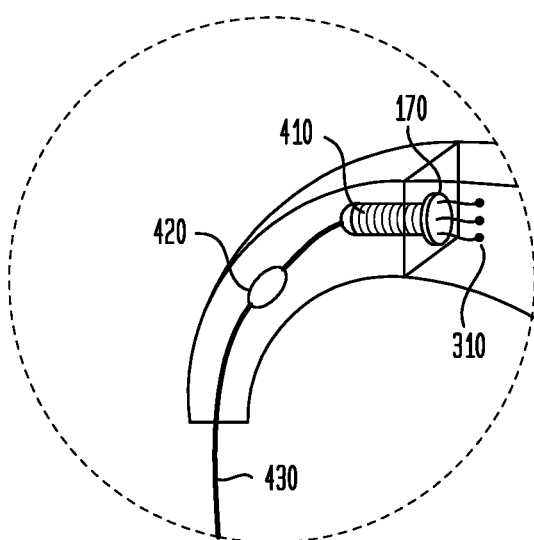
FIG. 2B illustrates a close-up view of a portion of the BTE prosthetic device of FIG. 2.

According to aspects of the present invention, an electromagnetic antenna is integrated with a mechanical connector which is used in BTE prosthetic device 100 to mechanically attach various components or other devices to the BTE prosthetic device. According to one embodiment of the invention, and referring to FIGS. 1 and 2, an electromagnetic antenna can be incorporated into a connector, shown as connector 170. In the specific illustrated embodiment of FIGS. 1 and 2, connector 170 of the BTE prosthetic device 100 is configured to mechanically attach an ear hook 180 to BTE prosthetic device 100. Connector 170 may also be configured to operate as, or function as, as an electromagnetic antenna for transmission of, or reception of signals between BTE prosthetic device 100 and one or more other components of the implantable hearing system.

Ear hook 180 provides a mounting means for holding BTE prosthetic device 100 behind the ear of the recipient. Connector 170 may include, for example, threaded attachment elements, a snap-lock or click-fit mechanism or any other removable mechanical fastening means now know or later developed for attaching connector 170 to BTE prosthetic device 100. In certain embodiments, one or more conducting wires 310 provide an electrical coupling between connector 170 and components of BTE prosthetic device 100, such as the printed circuit board of the BTE prosthetic device.

As noted, connector 170 may also be configured for electrical connection with an auxiliary device. For example, connector 170 may be provided with, or comprise, for example, a socket accepting a plug 410 of an auxiliary device 440, such as an earphone.

Figure 3A:
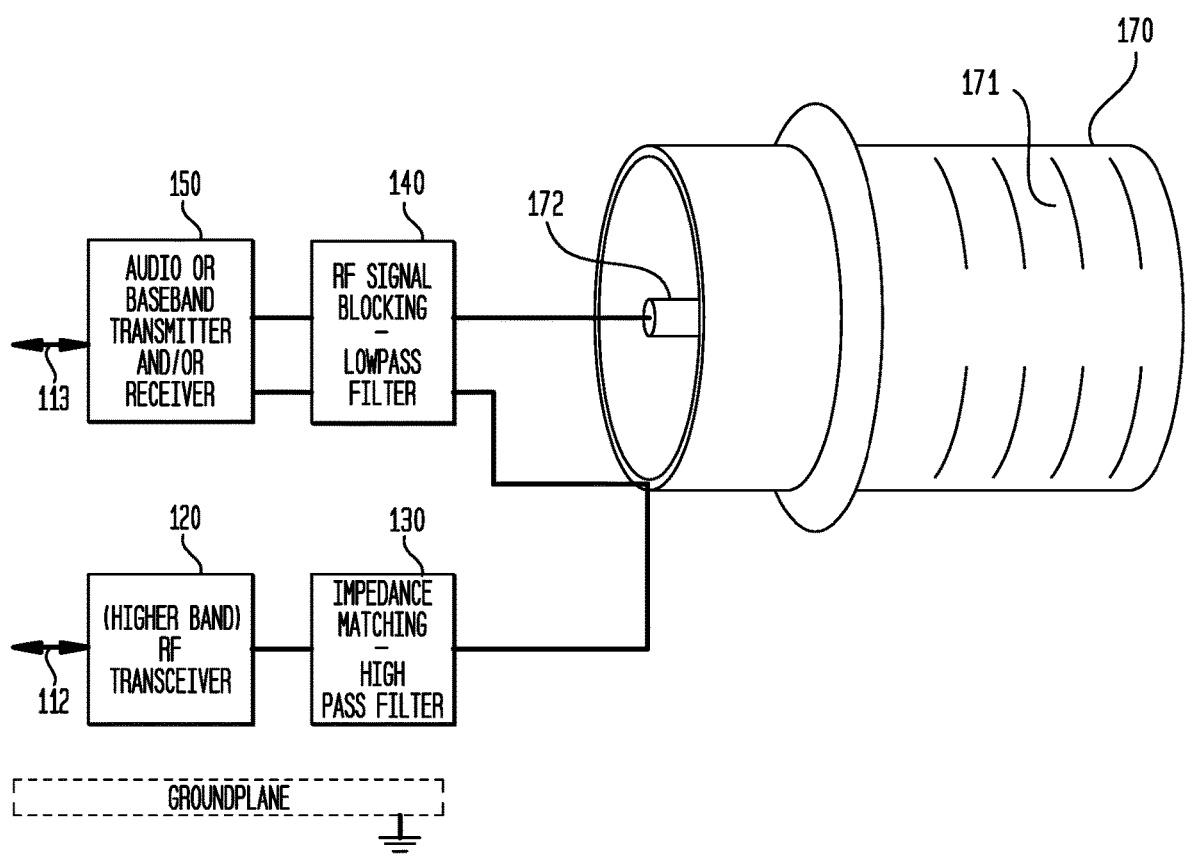
FIG. 3A illustrates a co-axial male connector in accordance with one embodiment of the present invention.
Figure 3B:
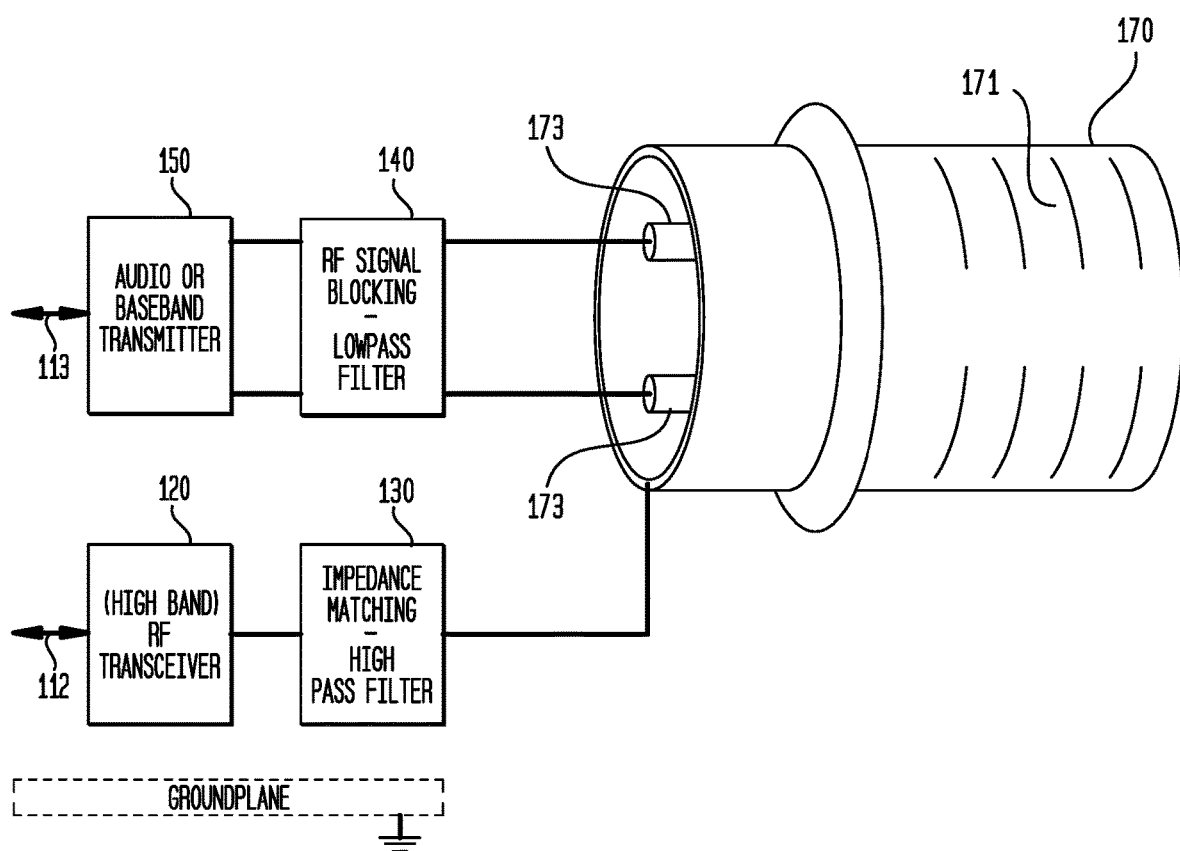
FIG. 3B illustrates a twin-axial male connector in accordance with one embodiment of the present invention.

Some possible embodiments of connector 170 are illustrated in FIG. 3. FIG. 3A illustrates connector 170 as a coaxial electrical and mechanical connector type. FIG. 3B illustrates connector 170 as a twin-axial electrical and mechanical connector type. In certain embodiments, connector 170 may comprise an outer body 171 which is cylindrical and may be made of an electrical conducting material.

In the embodiments of FIG. 3A, coaxial connector 170 comprises one electrically conductive receptacle 172, in addition to the conductive outer body 171. Hence, the outer body 171 and the receptacle 172, which are electrically shielded from each other, constitute an input or output jack for transmitting and/or receiving electrical signals, such as audio signals, to and from the attached auxiliary device 440. Therefore, BTE prosthetic device 100 may comprise an audio or baseband transmitter and/or receiver (transceiver) 150, linked at 113 to signal processor 110. Audio/baseband transceiver 150 is connected to the outer body 171 and to the receptacle 172 of connector 170.

The outer body 171 is configured to operate as, or function as, as part of an electromagnetic antenna for transmitting or receiving signals. As noted, connector 170 may be used by BTE prosthetic device 100 to transmit, or receive signals from, one or more other components of the implantable hearing system. In certain embodiments, outer body 171 operates as an open-ended wire, a monopole, stub, helix or helical wound coil, meander or dipole electromagnetic antenna. The electromagnetic antenna is operable in a variety of frequency ranges, including above 100 KHz, and in some embodiments in a frequency range above 30 MHz or 3 GHZ. As such, in the illustrated embodiments, connector 170 is configured for electrical connection of an auxiliary device to BTE prosthetic device 100 and for transmission and/or reception of signals between components of the hearing aid system.

BTE prosthetic device 100 may comprise an RF high band transceiver 120, linked via link 112 to signal processor 110. RF transceiver 120 is connected to the outer body 171. In order to improve the reception or transmission of power efficiency of outer body 171 as an antenna, an impedance matching circuit 130 may be provided between transceiver 120 and outer body 171. A high-pass or band-pass filter 130 and a low-pass or band-pass filter 140 ensure a separation of the radiated RF signals and the signals transferred over the jack combination 171/172. Hence, filter 140 blocks high RF band signals and prevents them from propagating to the transceiver 150 and high-pass filter 130 blocks low band signals (e.g. audio, baseband) and prevents them from leaking into transceiver 120.

Connector 170 may comprise multiple separate electrical conduction paths for conductive transmission of electrical signals. Likewise, outer body 171 of connector 170 may or may not transfer electrical signals. In certain embodiments, connector 170 protrudes from BTE prosthetic device 100.

FIG. 3B illustrates an additional embodiment of the present invention. As shown, the twin-axial connector 170 of FIG. 3B comprises two electrically conductive receptacles 173, in addition to a conductive outer body 171. Hence, the receptacles 173, which are electrically shielded from each other, constitute a jack for transmitting and/or receiving electrical signals, such as audio signals, to and from an auxiliary device 440 attached thereto. Therefore, BTE prosthetic device 100 may comprise an audio or baseband transmitter and/or receiver (transceiver) 150, linked at link 113 to signal processor 110. Audio/baseband transceiver 150 is connected to the receptacles 173.

In the embodiments of FIG. 3B, the outer body 171 may operate as an electromagnetic antenna similar to that described above with reference to FIG. 3A. Therefore, BTE prosthetic device 100 may comprise a high RF band transceiver 120, linked at link 112 to signal processor 110. RF transceiver 120 is connected to the outer body 171. In certain embodiments, to improve receive or transmit power efficiency of the antenna, an impedance matching circuit 130 is provided between transceiver 120 and the antenna (outer body) 171 for making the impedance of the antenna, as seen by the transceiver, real. A high-pass or band-pass filter 130 and a low-pass or band-pass filter 140 may ensure a separation of the radiated RF signals and the signals transferred over the jack 173. The low-pass and high-pass filters may be optional in the case of FIG. 3B, as the two types of signals (to/from transceivers 150 and 120) may not share the same electrical paths as in the case of FIG. 3A. However, radiated RF signals may be captured by the receptacles 173 and may interfere with the operation of the baseband transceiver 150. Likewise, the antenna 171 may capture low band signals. Hence, filter 140 blocks high RF band signals and prevents them from propagating to the transceiver 150 and high-pass filter 130 blocks low band signals and prevents them from leaking to transceiver 120.

A low band signal preferably comprises frequencies below or equal to about 100 KHz, while high RF band signals comprise signals situated in the radio spectrum above 100 KHz, such as, for example, 2.4 GHz. For the purposes of the present invention, high RF band signals are signals in the VHF (very high frequency), UHF (ultra high frequency), or higher frequency range. The low-pass filter 140 and the high-pass filter 130 may function as a band diplexer. The antenna 170 may be arranged to transmit or receive data such as telemetry, control data, signaling data and audio streaming.

Figure 4:
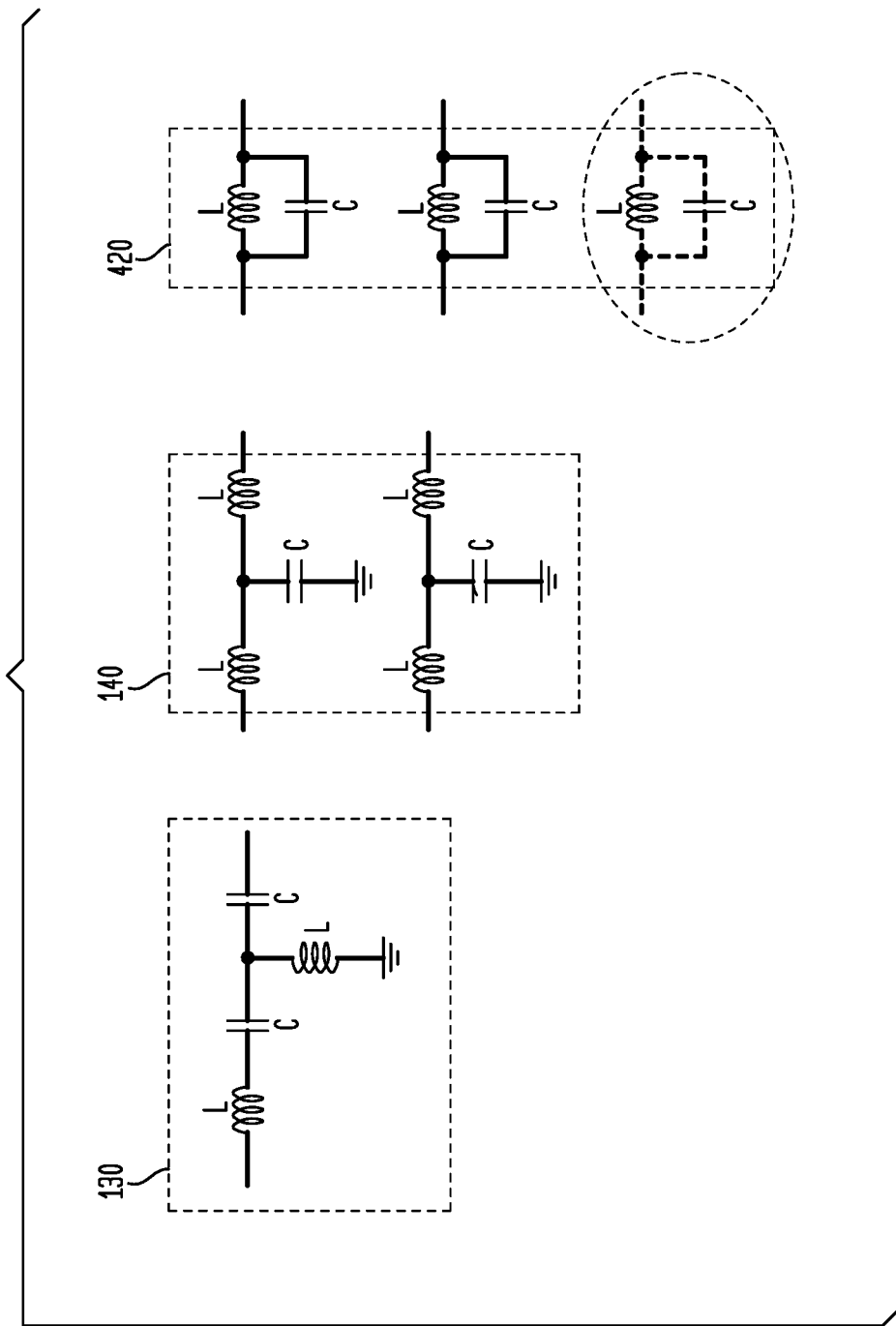
FIG. 4 illustrates embodiments of antenna impedance matching units and low-pass and high-pass filters in accordance with embodiments of the present invention.

FIG. 4 illustrates a possible implementation of the impedance matching circuit and high-pass filter 130 and the low-pass filter 140 in accordance with embodiments of the present invention. As shown in FIG. 4, such filters may comprise, for example, lumped resistors, capacitors and inductors, or other elements now know or later developed, the values of which may be chosen in function of the operating frequencies of the devices. The audio or baseband signals applied to or received from the auxiliary device are much lower in frequency than the RF signals radiated by the antenna. A third-order filtering may be sufficient in most cases.

Antenna impedance matching circuit 130 may be used to alter the effective electrical length of an antenna by matching it with additional capacitance or inductance. Antenna impedance matching circuit 130 tunes the radiating system of the antenna at the operational radio frequency, in order to obtain resonance. In one such case, the RF transceiver 120 sees the antenna as a purely resistive load. Such a matching circuit is optional.

Figure 5:
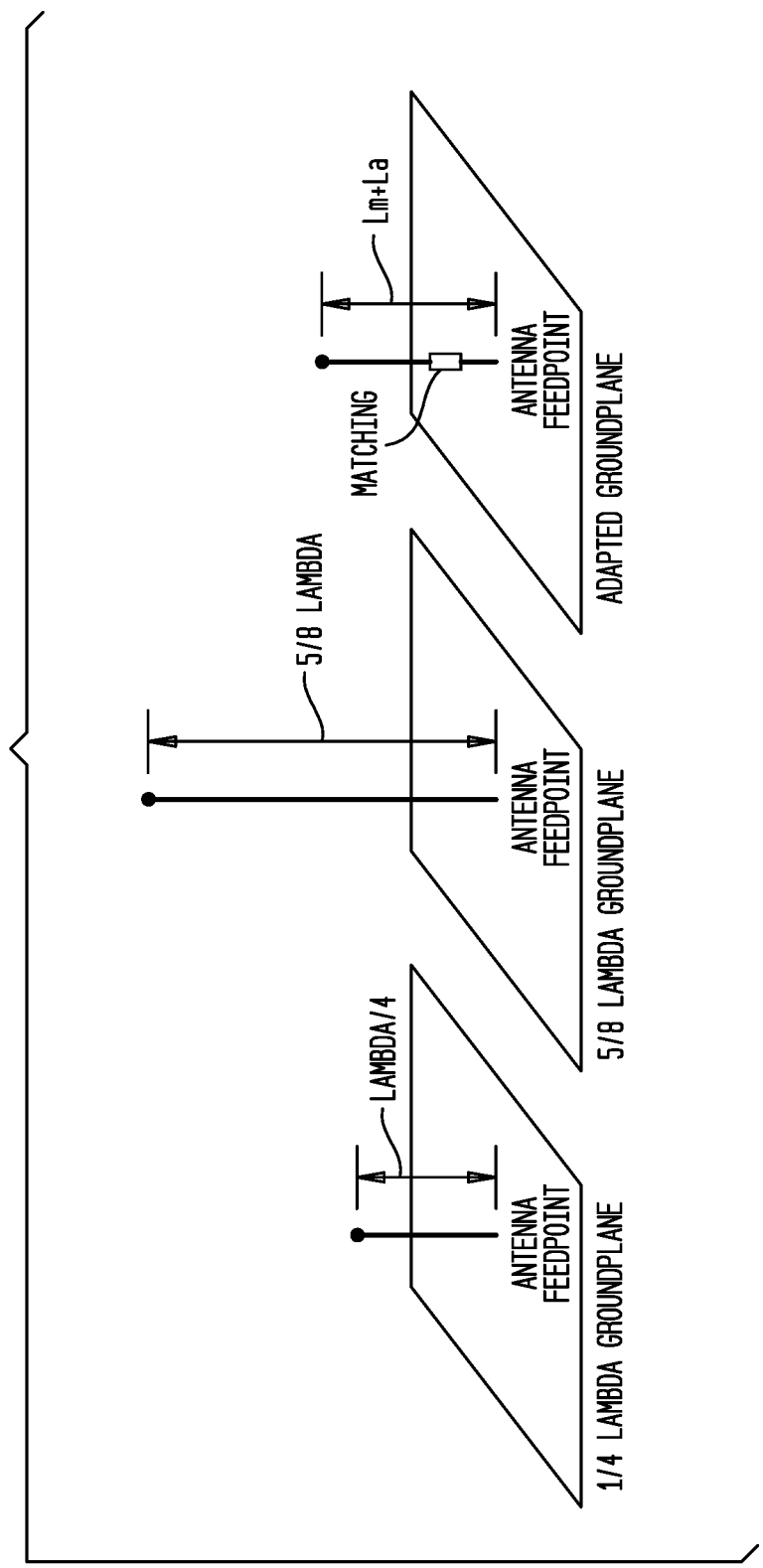
FIG. 5 schematically illustrates different matched ground-plane antennas.

As noted, antenna 171 may operate as an open-ended wire antenna, such as a monopole, a dipole, a groundplane, a helix, a helical wound, or a meander antenna. FIG. 5 shows a simplified representation of a quarter $\lambda$, a 5/8 $\lambda$ and a matched groundplane antenna.

The physical construction of antenna 171 of the present invention can be considered as a groundplane antenna, with the housing of BTE prosthetic device or its printed circuit board as ground plane element and the connector 170 as radiating or receiving element. From an antenna-matching viewpoint, it is preferable to choose the total physical length of the antenna (e.g. the length of the outer body 171 of connector 170) to $\lambda/4$ or 5/8 $\lambda$ with $\lambda$ the wavelength of the operating frequency of the antenna.

When the wavelength is very small, e.g. at 2.4 GHz, antenna matching is performed on the connector 170. At lower frequencies, an antenna with increased physical length is used. This may be achieved by incorporating, for example, into the auxiliary device which is attached to the BTE prosthetic device, an extension of antenna 170. Such an arrangement is illustrated in FIG. 1 with device 300.

In the illustrated embodiments, device 300 comprises all elements necessary for operation as an electromagnetic antenna, such as a ground plane and radiating/receiving elements. As such, device 300 is referred to as an auxiliary antenna device. The auxiliary antenna device 300 may be removably attached to the BTE prosthetic device 100 and comprises a connector plug 410 for acceptance by connector 170, the auxiliary device 440, a lead 430 between connector and auxiliary device and an optional antenna impedance matching circuit 420. The lead 430 is a naturally preferred object for use as radiating/receiving element and lends itself as an extension of antenna 170.

When auxiliary antenna device 300 is coupled to connector antenna 170, an antenna 500 is obtained with increased length over the antenna provided by connector antenna 170 alone. The total physical length of antenna 500 is the sum of the length Lm of the connector 170 (base antenna) and the length La of auxiliary antenna 300. The auxiliary antenna device 300 may comprise a matching circuit 420 in additional to the matching circuit 130 of connector 170.

The integration of a removable auxiliary antenna allows to improve radiating efficiency due to a physical extension of the radiating element. The auxiliary antenna devices 300 may allow antennas matched for different operating frequencies. The auxiliary antenna devices 300 may additionally allow antennas of different physical lengths for a same operating frequency. In the latter case, because of the different physical lengths, different impedance matching circuits should be implemented. Such embodiments, allow BTE prosthetic device 100 to be very versatile in the field of wireless communication and communicate with different devices over different RF bands.

Figure 6A:
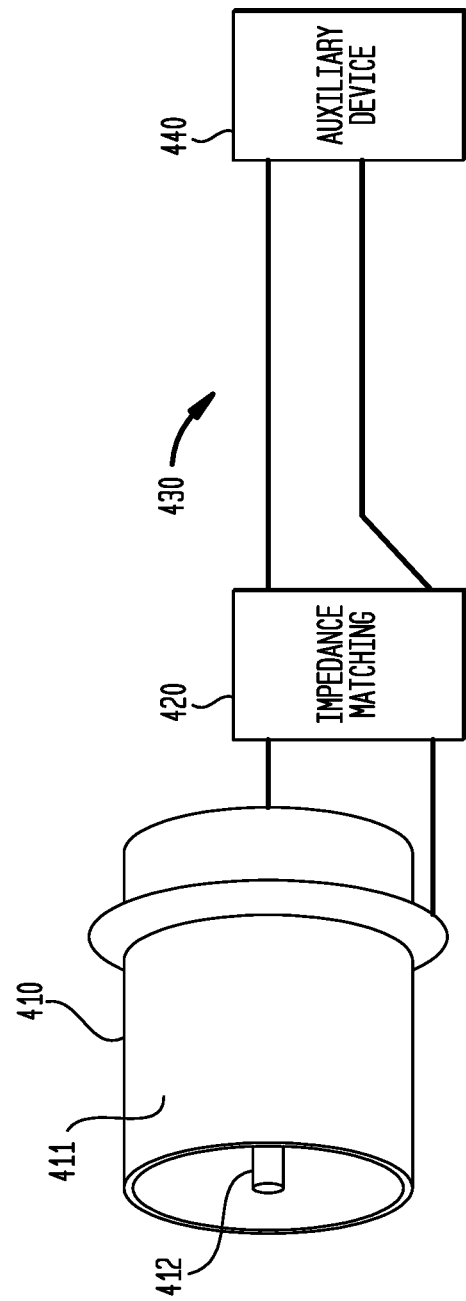
FIG. 6A illustrates a co-axial connector in accordance with one embodiment of the present invention.
Figure 6B:
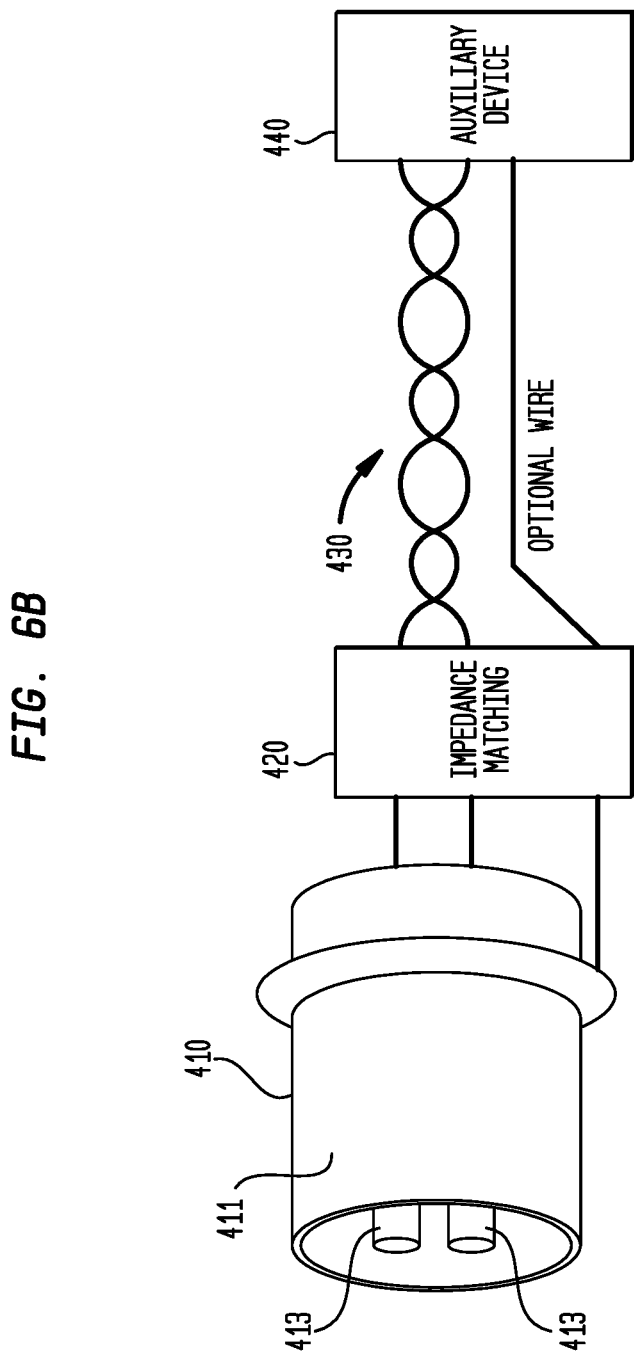
FIG. 6B illustrates a twin-axial connector in accordance with one embodiment of the present invention.

FIGS. 6A and 6B generally illustrates the components of auxiliary antenna device 300 in accordance with certain embodiments. Coaxial connector plug 410 of FIG. 6A is arranged for fitting into coaxial connector socket 170 of FIG. 3A. The twin-axial connector plug 410 is configured to fit into twin-axial connector socket 170 of FIG. 3B. A lead 430 comprising two or more conductive wires links connector plug 410 and impedance matching circuit 420, such as any of those shown in FIG. 4, to the auxiliary device 440. Lead 430 may conduct low-band electrical signals (e.g. audio signals) from BTE prosthetic device 100 to the auxiliary device 440 or vice versa.

In the case of a coaxial connector system 200, comprising socket 170 and plug 410 (FIGS. 3a and 6a), electrical connection with BTE prosthetic device 100 is obtained by electrical contact between receptacle 172 and plug 412, and between the outer bodies 171 and 411 of the connectors. In the case of a twin-axial connector system 200, comprising socket 170 and plug 410 (FIGS. 3b and 6b), the electrical connection with the BTE prosthetic device is obtained by electrical contact between the two receptacles 173 and plugs 413, and optionally additionally between the outer bodies 171 and 411 of the connectors.

Returning to FIG. 1, antenna 170, or the extended antenna 500, allows wireless communication in a radio frequency band between a BTE prosthetic device 100 and remote devices. Such devices may be a remote control unit 700, provided with an antenna 760 for wireless communication in the same frequency band. A bidirectional wireless communication link 710, 720 may be established between BTE prosthetic device 100 and remote control unit 700. The BTE prosthetic device 100 may also communicate wirelessly with cochlear implant 600, both through a magnetic induction link 810, 820 by aid of headpiece 116, and through a radio frequency electromagnetic link 610, 620 by the use of antennas 500 or 170 of the BTE prosthetic device and RF antenna 660 of the cochlear implant.

Figure 7:
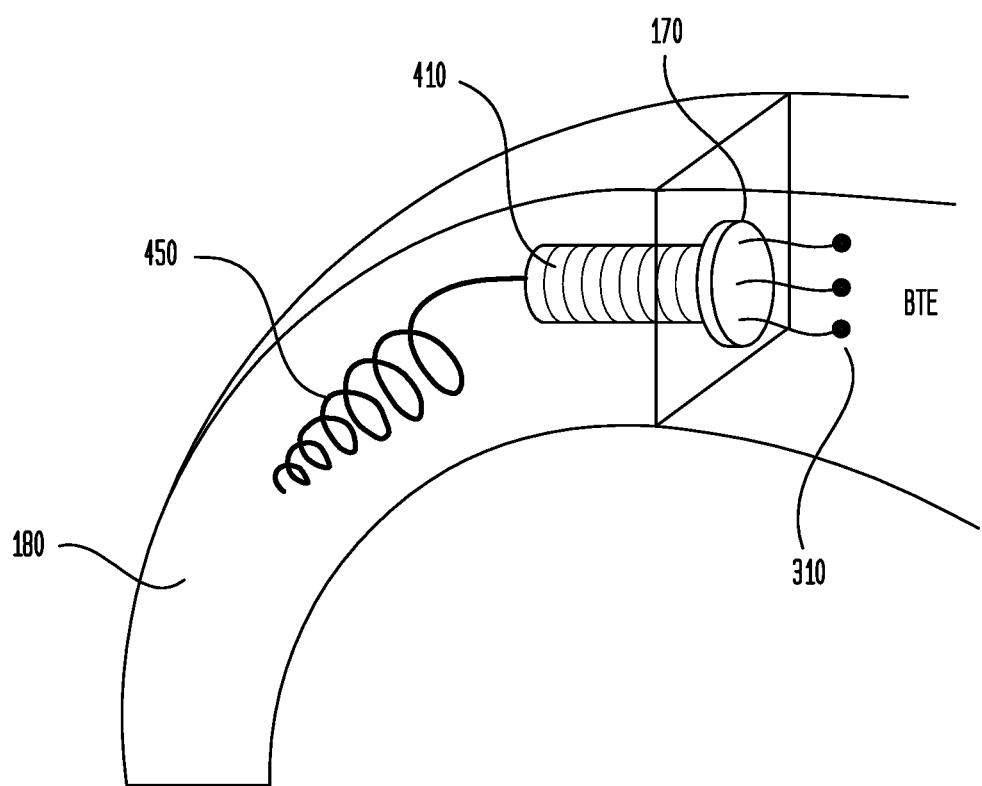
FIG. 7 illustrates a BTE prosthetic device having an ear hook mechanically attached thereto via a connector in accordance with embodiments of the present invention.

FIG. 7 illustrates an additional embodiment for an auxiliary antenna device 450 for use as extension of antenna 170. Antenna 450 is constituted by a helically wound antenna, and is incorporated into ear hook 180.

In accordance with certain embodiments, an auxiliary device may comprise an external plug-in device, such as an in-the-ear speaker. According to other aspects of the present invention, an antenna device comprises a second connector for fitting into the connector of BTE prosthetic device 100, an impedance matching circuit and a lead. The impedance matching circuit is tuned to the impedance of the lead, whereby the lead is operable as an extension of the electromagnetic antenna. The second connector is the counterpart of the connector of the hearing aid device. The second connector may be a plug or a socket.

Figure 8:
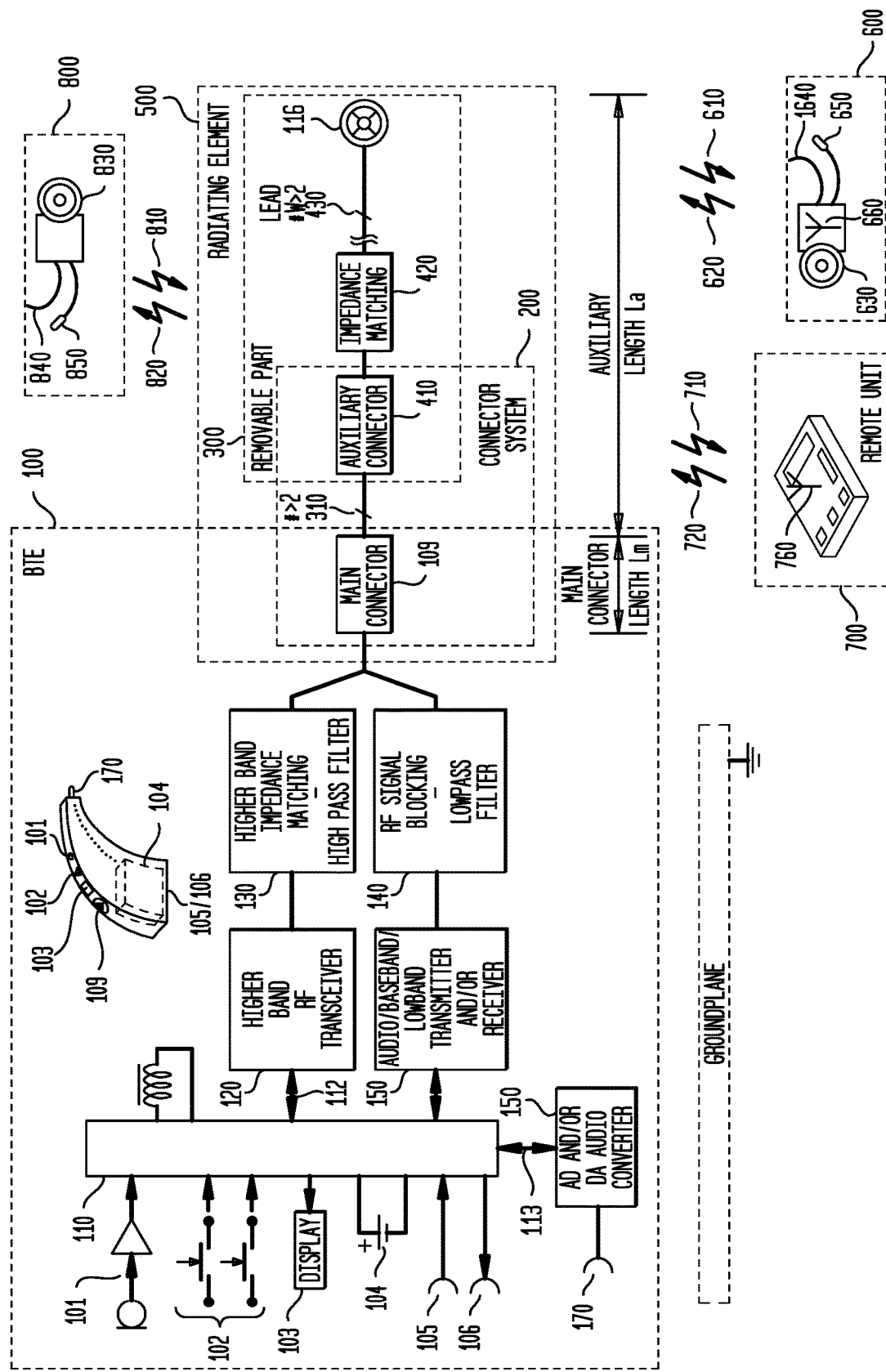
FIG. 8 is a block diagram of a BTE prosthetic device in accordance with embodiments of the present invention.

The antenna in accordance with embodiments of the present invention is not only restricted to connector 170 of an ear hook. FIG. 8 shows an alternative embodiment of the present invention wherein the antenna is incorporated into connector socket 109 of headpiece 116. In such embodiments, connector socket 109 may be implemented in a substantially similar manner as that described above with reference to connector socket 170. In the specific embodiments in which headpiece 116 is additionally used as an auxiliary RF antenna device, the removable device 300 may comprise an auxiliary connector 410 arranged for being accepted by connector 109, an impedance matching unit 420 and a headpiece 116, connected to the auxiliary connector 410 by a lead comprising two or more wires.

As discussed above with reference to FIG. 1, the BTE prosthetic device 100 may communicate wirelessly with an implant 600, which is provided with both a magnetic induction coil antenna 630 and an RF EM-field antenna 660. Coil antenna 630 may communicate with headpiece 116 when closely coupled. Communication over RF antennas 500 and 660 may be established simultaneously, or consecutively in time with the communication over antennas 116 and 630.

In the case that an implant, such as implant 800, is not provided with an RF antenna, wireless communication between BTE prosthetic device 100 and cochlear implant 800 may be established over a magnetic induction link 810, 820 using coil antennas 116 and 830, e.g. for transmitting stimuli signals to an electrode array 840 and/or actuator 850. Simultaneously, the BTE prosthetic device may communicate over antenna 500 with other devices, such as remote control unit 700.

While various embodiments of the present invention have been described above, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the following claims and their equivalents. For example, as one of ordinary skill in the art would appreciate, the present invention provides improved or at least alternative wireless communication possibilities compared to prior art devices and wireless communication methods. Active implantable medical devices envisaged by the present invention include, but are not limited to, cochlear implants, nerve stimulators, pace makers, glucose meters, and any other type of active implantable medical device requiring wireless communication.

U.S. Provisional Patent Application No. 60/924,800, filed on May 31, 2007, and U.S. Provisional Application No. 60/924,807, filed on May 31, 2007, are hereby incorporated by reference in their entirely herein. Similarly, all other patents and publications discussed herein are incorporated in their entirety by reference thereto.

The term "medical device" can refer to any instrument, apparatus, appliance, material or other article, whether used alone or in combination, together with any accessories or software for its proper functioning, intended to be used for human beings to, for example, diagnosis, prevention, monitoring, treatment or alleviation of disease or injury; to investigate, replace or modify of the anatomy or of a physiological process; or to control of conception, and which does not achieve its principal intended action by pharmacological, chemical, immunological or metabolic means, but which may be assisted in its function by such means. An 'active medical device' means any medical device relying for its functioning on a source of electrical energy or any source of power other than that directly generated by the human body or gravity. An 'active implantable medical device' is any active medical device which is intended to be totally or partially introduced, surgically or medically, into the human body or by medical intervention into a natural orifice, and which is intended to remain after the procedure.

The increased use of wireless communication in and miniaturization of active implantable medical devices (AIMDs) demands innovative, consistent and reliable designs of radio frequency (RF) system blocks and antennas. Antennas should be placed by preference outside any electrical or ferromagnetic shielding encapsulation to obtain a high efficiency in power transfer and high reliability in data transfer. The antenna characteristics for receiving energy are essentially the same as for sending due to antenna reciprocity. AIMDs are often shielded with a screening of titanium or other biocompatible material to decrease their vulnerability for trauma. The titanium RF shielding forces to position any type of antenna outside its shielding encapsulation.

A time-varying electrical current flowing in an antenna produces a corresponding electromagnetic field configuration that propagates through space in the form of electromagnetic waves. The total field configuration produced by an antenna can be decomposed into a far-field component, where the magnitudes of the electric and magnetic fields vary inversely with the distance from the antenna, and a near-field component with field magnitudes varying inversely with higher powers of the distance. The field configuration in the immediate vicinity of the antenna is primarily due to the near-field component (e.g. MI radio, Near Field Communication), while the field configuration at greater distances is due solely to the far-field component, also known as the electromagnetic far field propagation (electromagnetic radiation). The EM far field propagation can be physical explained by the decomposed E-field and H-field components of the EM field, maintaining each other and forming planar waves. The MI field is a non-propagating quasi-static magnetic field and has a very high field roll-off behaviour as a function of distance. Hence, the MI field is relevant only in the near-field. The electromagnetic (EM) field may be decomposed into a near-field component and a far-field component. The power of a plane wave in the EM far-field rolls off as one over the distance from the source squared. The EM near-field may further be decomposed into an EM reactive near-field and an EM radiating near-field. For the purpose of the present invention, the term "far-field" bears the meaning of "EM far-field", the term "near-field" may mean both an MI near-field and an EM near-field and the term "reactive near-field" may mean both an MI field and a reactive EM near-field.

A common type of antenna for active implantable medical devices is the coil antenna, also referred as closed-wire or loop antenna. An external coil antenna is coupled to the coil antenna of the implant to transfer upstream or downstream any required data such as telemetry, control data, signaling data and audio streaming.

The data transfer with those types of antennas occurs in the MI near-field and at lower frequencies(<15 MHz). In the MI near-field coil antennas are closely coupled and may also provide the AIMD with a power supply which enables operation or enables to charge an implanted battery if present.

US patent document 6766201 discloses an implantable medical device, such as a cardiac pacemaker, utilizing EM far-field data transfer by electromagnetic field propagation. Communication using far-field radiation can take place over much greater distances and makes the communication between the implant and external devices more convenient. The antenna of the implant is a classical open-ended monopole or dipole antenna.

Communication in the far-field classically utilizes an open-ended antenna tuned at a higher frequency band (typically>>50 MHz), such as a monopole or dipole antenna, relying on the propagating electromagnetic field characteristics. An open-ended wire antenna most efficiently radiates energy if the length of the antenna is the sum of a quarter wavelength and an integral number of half-wavelengths of the driving signal. A dipole antenna, for example, is a conductor which has a total length equal to half the wavelength of the driving signal with its feed point in the middle. A monopole antenna can be a conductor with a length equal to one-quarter the wavelength of the driving signal situated with respect to a reflecting ground plane so that the total emitted and reflected field configuration resembles that of the dipole antenna. As will be discussed below, an antenna matching circuit may be used to alter the effective electrical length of an antenna by adapting it with additional capacitance or inductance.

US patent document 6924 773 discloses an integrated dual band antenna, to be used externally to a recipient's body and which combines a magnetic induction shielded loop antenna and an electromagnetic radiation antenna. The shielded loop antenna may be used for communicating with an AIMD, while the electromagnetic radiation antenna is used for wireless communication with other external devices. The integration of both types of antennas is achieved by unshielding a part of the shielded loop antenna, inserting a low-pass filter and connecting the electromagnetic radiation antenna, provided with a high-pass filter, to said unshielded part.

The active implantable medical devices of the prior art either comprise means for wireless communication in the near-field (by magnetic induction) or means for wireless communication in the electromagnetic field. In the prior art, the problem of applying a wireless communication link with a medical implant both in the MI near-field and in the EM field is not tackled. Far-field communication may occur at higher frequency bands, which opens new possibilities and has additional benefits.

The additional placement of open-ended antennas next to the existing MI coil antennas outside the encapsulated shielded body of the AIMD to exploit the higher frequency bands would increase the AIMD size and probably decrease reliability. Moreover, as both antennas would have to be provided outside of the shielding encapsulation of the AIMD, this would result in an increased number of through-passages in the encapsulation for the antenna leads. Providing a leak-tight closure at these passages, around the antenna leads is a difficult matter.

In accordance with one embodiment of the present invention, an active implantable medical device is disclosed, comprising: an antenna and a band diplexer connected to the antenna, wherein the band diplexer comprises first filter means for a first signal to be transmitted and/or received in a first RF band and second filter means for a second signal to be transmitted and/or received in a second RF band, the second RF band being higher in frequency than the first RF band.

The present invention is related to active implantable medical devices and methods of wireless communication between external devices and said active implantable medical devices, which provide improved or at least alternative wireless communication possibilities compared to prior art devices and wireless communication methods. Active implantable medical devices envisaged by the present invention are: cochlear implants, nerve stimulators, pace makers, glucose meters, and any other type of active implantable medical device requiring wireless communication.

According to a first aspect of the invention, there is provided an active implantable medical device comprising an antenna and a band diplexer connected to said antenna. The band diplexer comprises first filter means for a first signal to be transmitted and/or received in a first RF band and second filter means for a second signal to be transmitted and/or received in a second RF band, said second RF band being higher in frequency than said first RF band.

Preferably, the antenna comprises one or multiple windings. More preferably, the antenna is a closed-wire antenna.

Preferably, the first filter means are connected in differential mode to the antenna and the second filter means are connected in common mode to the antenna.

Preferably, in the active implantable medical device according to the invention, the first signal is applied to the antenna in differential mode and the second signal is applied to the antenna in common mode. More preferably, the first signal is a reactive near-field signal and the second signal is a far-field signal.

Preferably, the antenna is arranged to transmit and/or receive the first signal over an MI near-field and arranged to transmit and/or receive the second signal over a radiating near-field or EM far-field.

Preferably, the antenna is arranged to operate simultaneously for transmitting or receiving the first signal and transmitting or receiving the second signal.

Preferably, the active implantable medical device according to the invention comprises: a first device arranged to receive said first signal in the first RF band and connected to said band diplexer, and a second device arranged to transmit said second signal in a second RF band and connected to said band diplexer. More preferably, the first device is connected to the band diplexer in differential mode and the second device is connected to the band diplexer in common mode. Even more preferably, in the active implantable medical device according to the invention the first device is further arranged for transmitting in the first RF band and the second device is further arranged for receiving in the second RF band.

In a preferred embodiment of the active implantable medical device according to the invention, both the first and the second devices are arranged for transferring unidirectionally power from said antenna towards the active implantable medical device using the reactive near-field. Preferably, the second device is arranged to indicate MI and/or EM field level or radio signal strength.

Preferably, in the active implantable medical device according to the invention, the frequencies of the first RF band are below or equal to 30 MHz and the frequencies of the second RF band are above 30 MHz. More preferably, the frequencies of the second RF band are above 50 MHz, even more preferably above 100 MHz. Preferably, the first signal is analogue and/or digital and the second signal is analogue and/or digital.

Preferably, the active implantable medical device according to the invention comprises an antenna matching unit arranged for impedance matching said antenna to an open-ended antenna for operation in the second RF band. The antenna matching unit is preferably connected to said band diplexer.

Preferably, in the active implantable medical device according to the invention, the first and/or second signal comprises one or more data from the group consisting of: telemetry, control data, signaling data and audio streaming.

According to a preferred embodiment, the active implantable medical device of the invention is a cochlear implant.

According to a second aspect of the invention, there is provided an external hearing aid device, comprising an antenna system and a band diplexer connected to said antenna system. Said band diplexer comprises first filter means for a first signal to be transmitted and/or received in a first RF band and second filter means for a second signal to be transmitted and/or received in a second RF band. Said second RF band is higher in frequency than said first RF band.

Preferably, in the external hearing aid device according to the invention, the antenna system comprises a closed-wire antenna. More preferably, the first signal is applied to the antenna in differential mode and the second signal is applied to the antenna in common mode.

According to a third aspect of the invention, there is provided a hearing aid system comprising: a cochlear implant of the invention and one or more external devices according to the invention.

Preferably, said one or more external devices comprise a sound processor device for behind the ear (BTE device). The sound processor device may process (i.e. filter, encode, etc.) airborne auditory signals captured by a microphone and convert them into stimuli signals suitable for use with the cochlear implant. The converted signals are transferred via a transcutaneous link to the cochlear implant. More preferably, the sound processor device for behind the ear comprises a connector for a closed-wire antenna external to said device for behind the ear for transcutaneous power transfer to the cochlear implant.

Preferably, in the hearing aid system according to the invention, said one or more external devices comprise a device for in the ear canal of a recipient.

Preferably, in the hearing aid system according to the invention, said one or more external devices comprise a remote control or handheld device.

According to a fourth aspect of the invention, there is provided a method of bidirectional wireless communication between an active implantable medical device and an external device, comprising the steps of: communicating unidirectionally from the external device to the implantable medical device over a first wireless link in a first RF band in the MI near-field and communicating unidirectionally from the implantable medical device to the external device over a second wireless link in a second RF band in the EM-field, preferably the EM far field.

According to a fifth aspect of the invention, there is provided a method of bidirectional wireless communication between an external hearing aid device and a second external device, comprising the steps of: communicating unidirectionally from the second external device to the external hearing aid device over a first wireless link in a first RF band in the MI near-field and communicating unidirectionally from the external hearing aid device to the second external device over a second wireless link in a second RF band in the EM-field, preferably the EM far field.

Preferably, in the methods according to the invention, said second RF band is higher in frequency than said first RF band.

Embodiments of the present invention will now be described in detail with reference to the attached figures, the invention is not limited thereto but only by the claims. The drawings described are only schematic and are non-limiting. In the drawings, the size of some of the elements may be exaggerated and not drawn on scale for illustrative purposes. The dimensions and the relative dimensions do not necessarily correspond to actual reductions to practice of the invention. Those skilled in the art can recognize numerous variations and modifications of this invention that are encompassed by its scope. Accordingly, the description of preferred embodiments should not be deemed to limit the scope of the present invention.

Furthermore, the terms first, second and the like in the description and in the claims are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

Moreover, the terms top, bottom, left, right, over, under and the like in the description and the claims are used for descriptive purposes and not necessarily for describing relative positions. The terms so used are interchangeable under appropriate circumstances and the embodiments of the invention described herein can operate in other orientations than described or illustrated herein. For example "left" and "right" from an element indicates being located at opposite sides of this element.

It is to be noticed that the term "comprising", used in the claims, should not be interpreted as being restricted to the means listed thereafter; it does not exclude other elements or steps. Thus, the scope of the expression "a device comprising means A and B" should not be limited to devices consisting only of components A and B. It means that with respect to the present invention, the only relevant components of the device are A and B.

The present invention overcomes the shortcomings of prior art devices by integrating an open-ended (EM-field) antenna into a closed-wire (near-field) antenna so as to obtain one single physical antenna which is able to operate over two separate frequency bands. The combined antenna of the invention allows to establish bidirectional data communication links over a first, lower radio frequency band and over a second, upper radio frequency band. The two bands may be used simultaneously or consecutively in time for bidirectional communication between the AIMD and external devices operating in the lower RF band and the upper RF band. In an equally preferred embodiment of the invention, the combined antenna allows to establish a forward unidirectional data communication link over a first, lower RF band (e.g. towards an AIMD) and a backward unidirectional data communication link over a second, upper RF band (e.g. from the AIMD towards an external device).

The first, lower radio frequency band lies preferably below 30 MHz, more preferably below 15 MHz. The second, upper frequency band lies preferably well above 15 MHz, more preferably well above 50 MHz (e.g. on the order of a few GHz). For the purposes of the present invention, the upper RF band signals are signals in the VHF (very high frequency), UHF (ultra high frequency), or higher frequency range.

Figure 9:
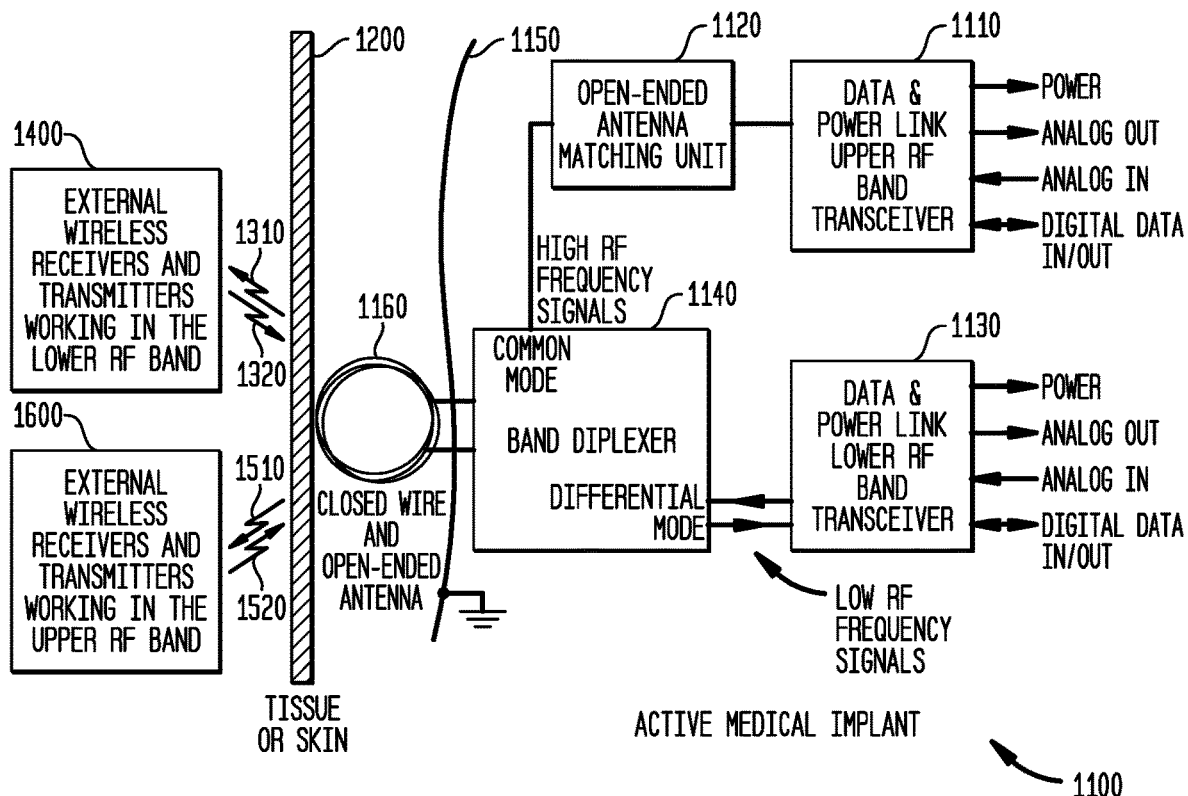
FIG. 9 is a block diagram showing the active implantable medical device according to the present invention.

FIG. 9 shows an implantable antenna for an active implantable medical device 1100. The antenna is physically formed by a closed electrical loop with one or multiple windings 1160. The antenna has both the properties of a closed-wire loop antenna and of an open-ended wire antenna. The antenna is provided outside of a shielding encapsulation 1150 of the AIMD and is implanted beneath the skin 200 of a recipient.

In order to perform its dual band role, the antenna 1160 is connected to a band diplexer 1140. The antenna 1160 operates furthermore in combination with a ground plane 1150, which may be the shielding encapsulation 1150, an open-ended antenna matching unit 1120, an upper band transceiver 1110 and lower band transceiver 1130. A transceiver comprises a receiver and transmitter and processes the radio frequency signals that are received or that are to be transmitted. Transceivers 1110 and 1130 may be provided with inputs and outputs for receiving and transmitting analogue data, inputs and outputs for receiving and transmitting digital data and with an output for transmitting power signals to the implant. Either one or both the transceivers may also be a receiver or a transmitter only.

For communication over the upper RF band, the antenna behaves as a kind of monopole element with an asymmetrical RF power hot-feed point at both coil ends and feeder ground attached to the ground plane 1150. The ground plane could be the electrical shielding of the implant encapsulation or any printed circuit board (PCB) ground if the implant encapsulation is unshielded. The matching unit 1120 puts the antenna system for the upper RF band into resonance and optimum impedance.

For communication over the lower RF band, the antenna behaves as a closed-wire loop preferably with a symmetrical feed point. A current from the lower RF band transmitter 1130 through the coil 1160 generates a magnetic field. The Biot-Savart law describes this magnetic field set up due to a steady flowing line current in a current wire element or steady current density (magneto-statics). The signal applied to the lower RF band receiver 1130 is a voltage induced in the loops of the coil 1160 that is proportional to the change of magnetic flux. This is based on Faraday's law.

Figure 10:
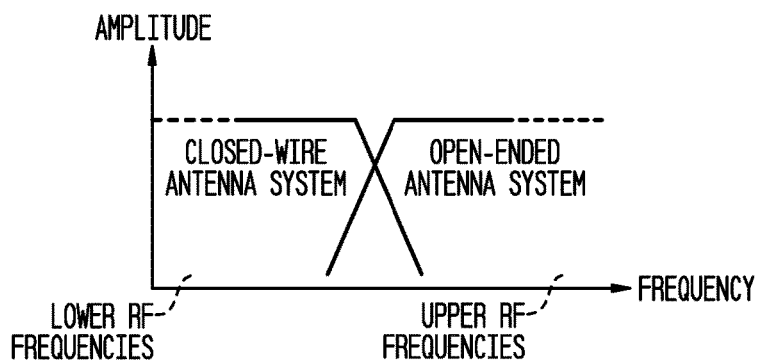
FIG. 10 is a representation of the frequency-amplitude characteristics of the band diplexer (low-pass and high-pass characteristic).

The band diplexer 1140 comprises a filter for the upper radio frequency band, such as a high-pass or a band-pass filter and a filter for the lower radio frequency band, such as a low-pass or a band-pass filter. That creates a separation or isolation between the low RF signals (lower RF band) and the high RF signals (upper RF band). This allows simultaneous operation over both frequency bands. Transmitted signals 1510 from the upper RF band transmitter 1110 towards external devices 1600 will not interfere with signals 1320 from external devices 1400 working in the lower RF band towards the lower RF band receiver 1130. Transmitted signals 1310 from the lower RF band transmitter 1130 towards external devices 1400 will not interfere with signals 1520 from external devices 1600 working in the upper RF band towards the upper RF band receiver 1110. This signal separation is illustrated in FIG. 10 as a frequency-amplitude characteristic.

Figure 11:
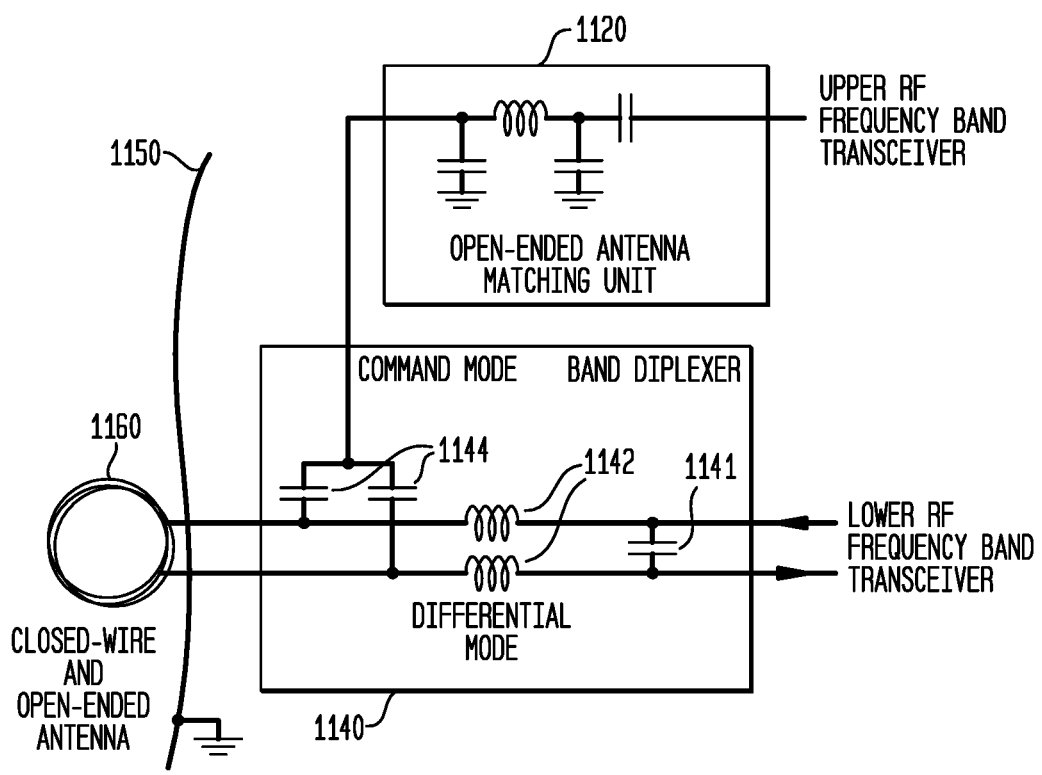
FIG. 11 represents the band diplexer and the open-ended antenna matching circuit for the antenna of the invention.

Referring to FIG. 11, the band diplexer 1140 comprises upper RF band coupling elements, preferably two low-valued capacitors 1144. These will block the lower RF signals for the upper RF transceiver system 1110. Additionally, the band diplexer 1140 comprises lower RF band coupling elements, preferably two low-valued inductors 1142. These will block the upper RF signals for the lower RF transceiver system 1130. Optionally, a capacitor 1141 can be used to obtain resonance at the lower RF band for improving power and data transfer efficiency. The value of the capacitors and the inductors and other electrical elements may be chosen in function of the frequency bands used.

A major benefit using this band diplexer topology is the existence of a common and differential mode. The differential mode is used for the closed-wire antenna system in the lower RF band, whereas the common mode is used for the open-ended antenna system in the upper RF band. Because of the different modes of operation, additional electrical isolation between the two transceiver systems 1110 and 1130 can be obtained.

The communication link over the lower RF band (1310 and 1320 of FIG. 9) is based on magnetic induction and is preferably below 30 MHz, more preferably below 15 MHz. This link utilizes the non-propagating quasi-static magnetic field. The magnetic field has a very high roll-off behavior as a function of distance.

The communication link over the upper RF band (1510 and 1520 of FIG. 9) is based on electromagnetic field propagation and is preferably higher than 30 MHz, more preferably much higher than 50 MHz. The power of a plane wave in the far-field rolls off as one over the distance from the source squared.

The medical implant device 1100 is able to communicate wirelessly with other devices over an upper RF band and a lower RF band, simultaneously or consecutively in time. The communication link over the lower RF band is a magnetic induction link, operating in the reactive near-field. The communication link over the upper RF band may operate in the reactive near-field, the radiating near-field and/or in the propagating far-field. Operation in the reactive near-field necessitates that the antennas of the implant and the communicating device be arranged in close proximity.

A power transfer from external devices 1400 and 1600, operating in the reactive near-field at respectively lower RF bands and upper RF bands towards the AIMD 1100, over the lower RF band 1320 or upper RF band 1520, can be established with a coil antenna 1160 connected to a band diplexer 1140, in combination with a ground plane for the upper RF band 1150, an open-ended antenna-matching unit 1120, an upper band transceiver 1110 and a lower band transceiver 1130.

In the reactive near-field, where coils are magnetically closely coupled, the external device 1400 could transfer sufficient power over the lower frequency band 1320 towards the AIMD to provide the implant with electrical energy enabling operation or charging of its implanted battery if present.

Figure 12:
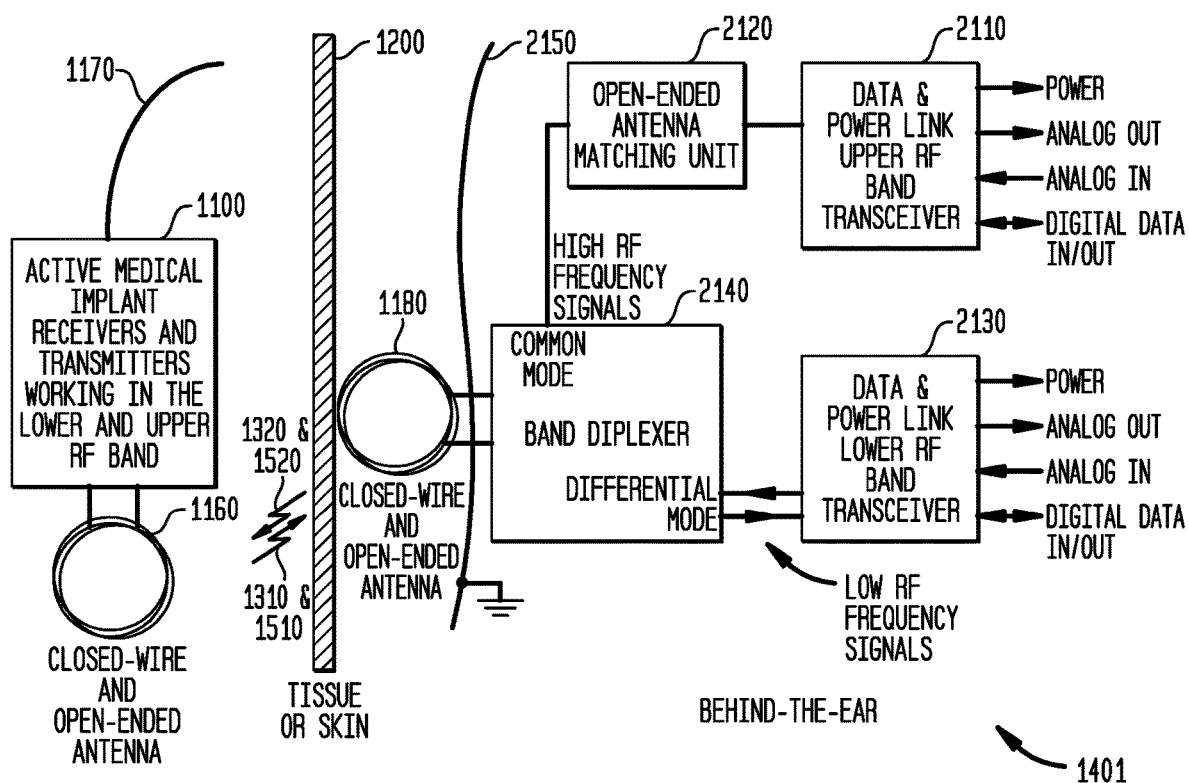
FIG. 12 is a block diagram showing the embodiment according to the third object of this invention.
Figure 13:
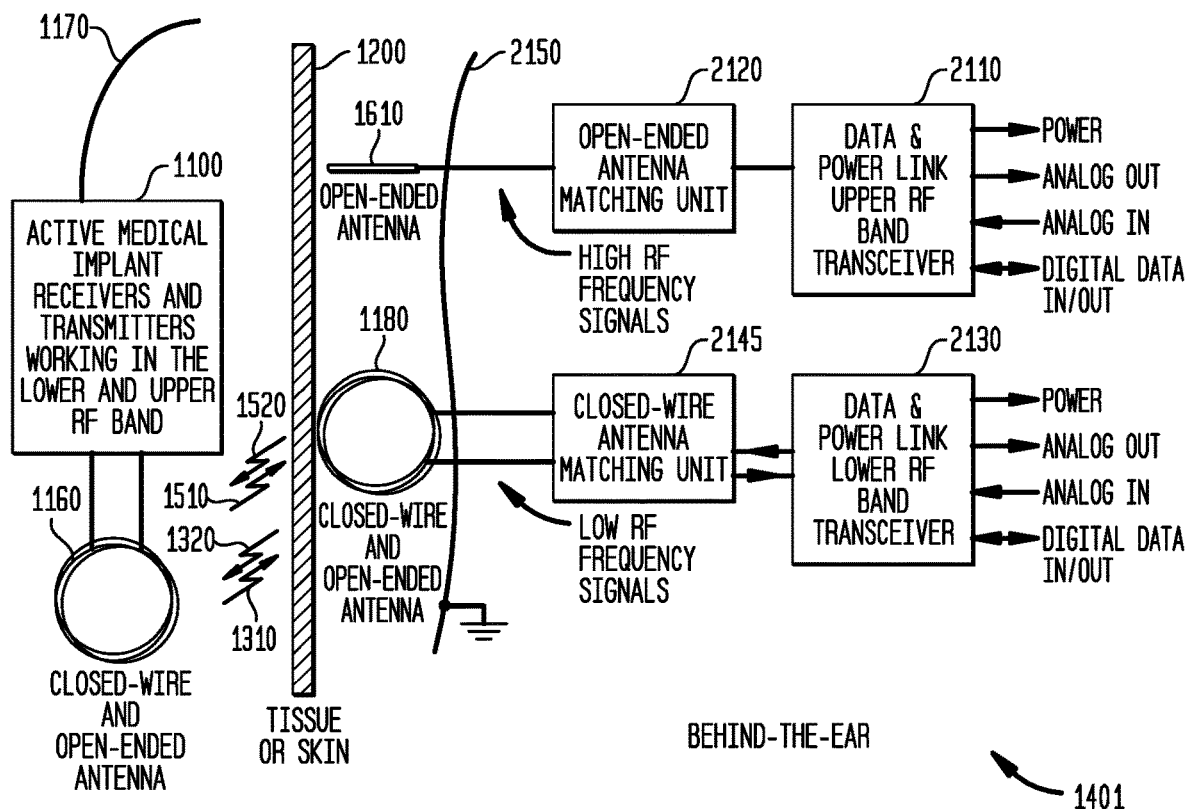
FIG. 13 is a block diagram showing the embodiment according to the third object of this invention.

According to another aspect of the invention, an external device may communicate with an active implantable medical device 1100 of the invention over a first, lower radio-frequency band and/or a second, upper radio frequency band. Referring to FIG. 12 and FIG. 13, the communication link between implant device 1100 and external device 1401 over the lower RF band (1310, 1320) is based on magnetic induction. The lower RF band communication link 1310 and 1320 utilizes the non-propagating quasi-static magnetic field (reactive near-field). The communication link 1510 and 1520 over the upper RF band may operate in the near-field and/or in the propagating far-field (electromagnetic field propagation).

FIG. 12 shows an antenna 1180 for an external device 1401 (e.g. a behind-the-ear device), physically formed by a closed electrical loop with one or multiple windings. Antenna 1180 has the properties of both a closed-wire loop antenna and an open-ended wire antenna. The antenna 1180 is connected to a band diplexer 2140. The antenna 1180 operates furthermore in combination with a ground plane 2150, an open-ended antenna matching unit 2120, an upper band transceiver 2110 and lower band transceiver 2130. The ground plane can be the electrical shielding of the encapsulation of external device 1401 or a printed circuit board ground. The configuration of the band diplexer 2140 and antenna matching unit 2120 may be similar to that of band diplexer 1140 and antenna matching unit 1120 of the implant 1100. Hence, band diplexer 2140 may comprise a filter for the lower RF band signals (differential mode signals) and a filter for the upper RF band signals (common mode signals).

The antenna 1180 allows to establish bidirectional data communication links over a first, lower radio frequency band (1310, 1320) and over a second, upper radio frequency band (1510, 1520). The two bands may be used simultaneously or consecutively in time for bidirectional communication between external device 1401 and the AIMD 1100 or other devices. In order to use the lower RF band magnetic induction link, the antenna 1180 of the external device should preferably be located at short range of antenna 1160. Lower RF band transceiver 2130 may be a transmitter or receiver only. Upper RF band transceiver 2110 may be a transmitter or receiver only.

As shown in FIG. 13, in order to communicate with the AIMD 1100 of the invention, an external device should comprise either one or both antennas 1480 or 1610.

Antenna 1480 is a closed-wire antenna and operates in a lower RF band according to a non-propagating quasi-static magnetic field (magnetic induction). Closed-wire antenna 1480 is connected to a closed-wire antenna matching unit 2145 for adjusting the impedance and resonance of the antenna and with a lower RF band transceiver 2130. Transceiver 2130 may also be a transmitter or a receiver only.

Antenna 1610 is an open-ended antenna and operates in a higher RF band according to electromagnetic field propagation. Open-ended antenna 1610 is connected to an open-ended antenna matching unit 2120 and to an upper RF band transceiver 2110. Transceiver 2110 may also be a receiver or a transmitter only. The open-ended wire antenna 1610 operates in combination with a ground plane 2150 and may be a monopole, stub, helix or helical wound coil, meander or dipole antenna. In case of a dipole antenna, the use of a ground plane 2150 becomes optional.

Transceivers 2110 and 2130 may be provided with inputs and outputs for receiving and transmitting analogue data, inputs and outputs for receiving and transmitting digital data and with an input for transmitting power signals to the implant.

Figure 14:
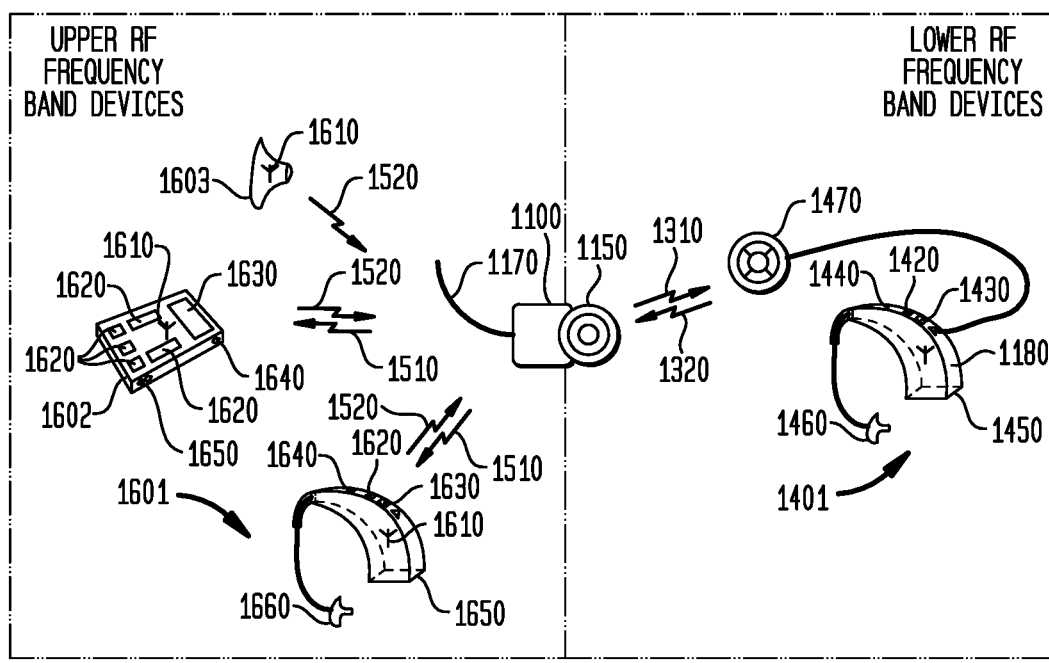
FIG. 14 represents a hearing aid system comprising an active implantable medical device (AIMD) and external devices.

FIG. 14 illustrates an embodiment of the AIMD of the invention as a cochlear implant 1100 in a hearing aid system. The cochlear implant 1100 is an implantable hearing aid device comprising a cochlea stimulating electrode 1170 that stimulates by applying electrical signals the auditory nerves of the cochlea or brainstem. Depending on cause of recipient's deafness, a mechanical implantable actuator stimulating middle or inner parts of the ear can be placed in conjunction or as alternative. The cochlear implant is implanted beneath the human skin, near the left or right ear. The cochlear implant comprises a combined open-ended and closed-wire antenna 1160, and an implantable battery (not shown). The implant communicates with several external devices (1401, 1601, 1602, 1603) as summed hereafter.

A first type of external device is behind-the-ear (BTE) device 1401, which comprises a dual-band coil antenna 1180 according to the one of FIG. 12. Antenna 1180 is a combined open-ended and closed-wire antenna similar to the principle of the combined coil antenna of an implant. BTE device 1401 allows wireless bidirectional data transfer (1310, 1320) over the lower RF band. Therefore, either coil antenna 1180 or headpiece 1470 may be used. Coil antenna 1180 creates a magnetic induction link with the dual-band coil antenna 1160 of the implant. Headpiece 1470 is a coil antenna, which may be connected externally to the BTE device 1401. This allows to attach headpiece 1470 in close proximity to the combined coil antenna 1160 of the implant device 1100. Attachment or fixation between headpiece 1470 and antenna coil 1160 of the implant may be done by a permanent magnet. Headpiece 1470 is particularly useful for wireless transcutaneous power transfer over the lower frequency band 1320.

The behind-the-ear device 1401 may further comprise a microphone system 1440, human interface controls and buttons 1420, a small display 1430, in-the-ear speaker 1460, digital and analogue inputs and outputs 1450, signal processing circuits, memory and batteries.

A second type of behind-the-ear device 1601 is capable of communicating wirelessly over an upper RF band. The bidirectional data transfer over that upper RF band uses electromagnetic field propagation (1510, 1520). Therefore, BTE device 1601 comprises an open-ended antenna 1610, e.g. of monopole or dipole type. BTE device 1601 may further comprise a microphone system 1640, human interface controls and buttons 1620, a small display 1630, an in-the-ear speaker 1660, digital and analogue inputs and outputs 1650, signal processing circuits, memory and batteries. BTE device 1401 may equally well act as BTE device 1601, as it comprises a dual band antenna 1180 of the invention.

Another type of external device is a remote control or handheld device 1602, which incorporates a receiver and transmitter system with antenna 1610 for bidirectional wireless communication (1510, 1520) in the upper RF band. The remote control 1602 may comprise a microphone system 1640, human interface controls and buttons 1620, a display 1630, digital and analogue inputs and outputs 1650, signal processing circuits, memory and batteries.

An additional type of external device is an in-the-ear device 1603, comprising a transmitter system with antenna 1610 for unidirectional wireless communication 1520 in the upper RF band. The in-the-ear device 1603 may comprise a microphone system, human interface controls and buttons, signal processing circuits, memory and batteries.

The radiating elements (antennas) 1610 of the second type of behind-the-ear device 1601, the remote control 1602 and in-the-ear device 1603 are open-ended wire antennas such as monopole, stub, helix or helical wound coil, meander or dipole antennas. In case of a dipole antenna, no ground plane is needed.

Figure 15:
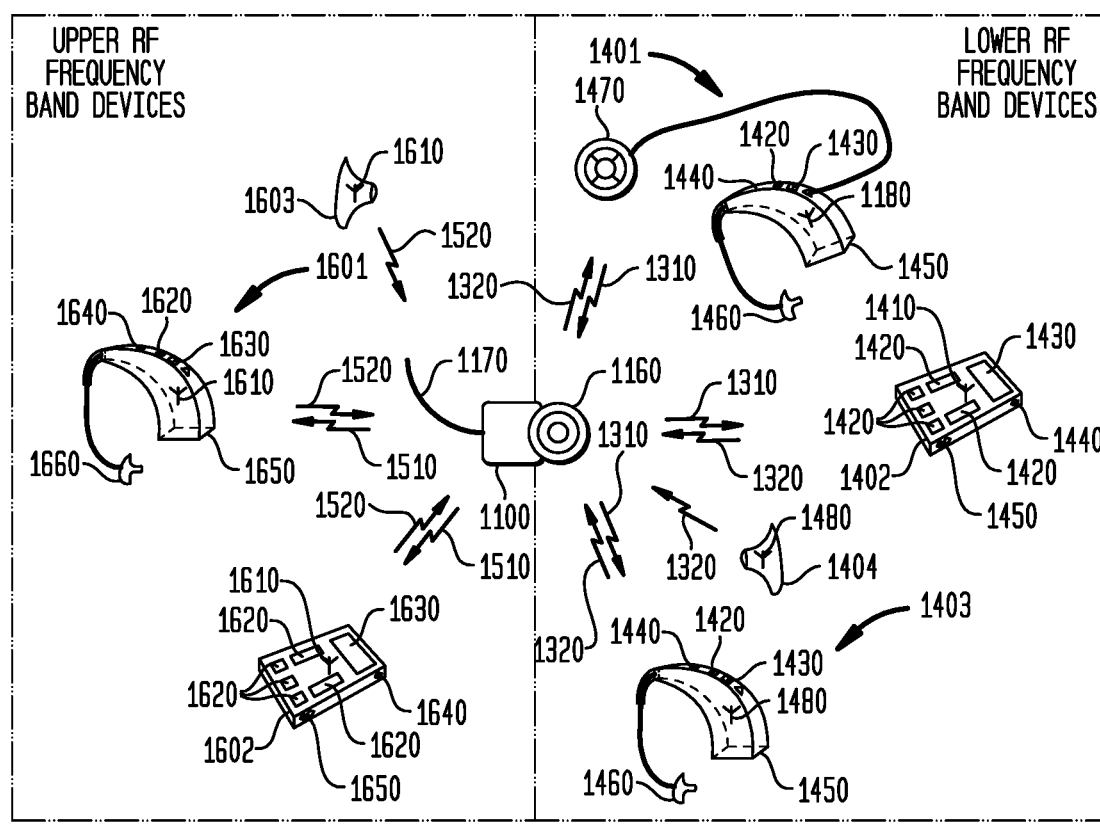
FIG. 15 represents another hearing aid system comprising an active implantable medical device (AIMD) and external devices.

FIG. 15 illustrates other system combinations. A remote control 1402, a BTE device 1403 and an in-the-ear device 1404 may communicate uni- or bidirectionally with implant 1100 over a lower RF band by using a coil antenna 1480 to create a magnetic induction link with the dual-band coil antenna 1160 of the implant. Therefore, remote control 1402, BTE device 1403 and in-the-ear device 1404 each comprise a closed-wire antenna 1480 for wireless communication over a lower RF band.

Since the implant can operate simultaneously in the lower and upper RF bands by implementation of two transceivers, bilateral or binaural communication between two BTEs or even two implants is supported in one RF band, whilst having a supplementary communication link in the other RF band. External devices 1401, 1402, 1403 and 1404 may also communicate with each other via the lower RF link. External devices 1601, 1602, 1603 may communicate with each other via the upper RF link. A remote unit 1402 or 1602 may communicate with the implant 1100 via a BTE device 1401 or respectively 1403 or 1601. Bilateral communication comprises telemetry, control data, signaling data and audio streaming.

The wireless communication links of the present invention may be used for controlling and programming medical implant devices. The two-band communication capabilities of the implant devices of the invention allow to obtain an energy optimization. Battery cells supply all kinds of implant devices with power, providing the recipient with limited duration autonomy. Since recipients and the market demand for longer system autonomy and miniaturization, an optimized design of the wireless communication link with very low power consumption is required.

According to an additional aspect of the invention, a method of wireless communication is provided between any AIMD of the invention and an external device, such as a remote control unit or a remote programmable unit. The present method allows to reduce energy consumption of the AIMD. According to the method, the forward wireless communication from the external device to the AIMD operates over the lower band magnetic induction. link (near-field communication) and the backward wireless communication from the AIMD to the external device operates over the upper band electromagnetic field propagation link (far-field communication). Over a long range, an EM-field wireless communication uses a lower amount of energy resources than an MI field wireless communication. Hence, the method allows to reduce power consumption of the AIMD of the invention.

Furthermore, in case that the forward communication takes place over the magnetic induction link only, an upper RF band receiver is not required on the AIMD. In case that the backward communication takes place over the electromagnetic field propagation link only, a magnetic induction transmitter is not required on the AIMD. This allows to save space on the AIMD.

According to a further aspect of the invention, a method of wireless communication is provided between a fitting system and a hearing aid system. Since recipients of hearing aid systems have different auditory defects, each hearing aid device must be adjusted, "fitted" or "mapped" specifically to an individual's needs and his/her responses to sound. This fitting process requires an initial appointment with an audiologist at a clinical implant centre. The fitting process adjusts the "map" as the brain adapts to incoming sound. Wireless fitting or mapping offers benefit to the audiologist and to the recipients, especially when the recipient is a child. The method of the invention optimizes the power consumption at recipient's side during fitting sessions by selecting a dedicated wireless technology for forward link and another dedicated wireless technology for back-data link.

The fitting system generally is a remote, external programmable unit, such as a PC, provided with a wireless communication link with the recipient's hearing aid system. The remote programmable unit can easily increase the magnetic field presented to the target devices (BTE device or cochlear implant). This reduces amplification and power consumption for the target (hearing aid) device. By way of example, the remote programming unit (RPU) is capable of supplying more power to its MI transmitter because the RPU is connected to the mains (electrical wired power distribution 110 Vac/230 Vac) and hence has the availability of quasi unlimited power. The power consumption of the transceiver of the hearing aid system (e.g. transceiver 2110) hence can be made much lower than the power consumption of the transceiver of the fitting or RPU system. Moreover, due to the increased magnetic field, the target device need not be equipped with a highly selective receiving filter for the MI receiver, because a third party's MI interference field is strongly attenuated (inversely proportional to $r^3$). This allows to save space on the target device (BTE device, cochlear implant).

A further reduction in power consumption of the target device—the hearing aid device (e.g. a BTE device or a cochlear implant)—can be obtained by having the forward wireless communication link from the fitting system to the hearing aid device established through magnetic induction (near-field communication) and the backward wireless communication link from the hearing aid device to the fitting system established through electromagnetic field propagation (far-field communication). Moreover, in case the far-field communication is always established unidirectionally (i.e. backward), a far-field receiver and selective receiving filter may be absent on the hearing aid device. This allows to save space on the BTE device or the cochlear implant.

The method of the invention can equally be applied more in general to BTE devices of the invention. In the case of wireless communication between a BTE device and a second external device, such as a remote control unit or a remote programmable unit, the forward wireless communication from the second external device to the BTE device operates over the lower band magnetic induction link (near-field communication) and the backward wireless communication from the BTE device to the second external device operates over the upper band electromagnetic field propagation link (far-field communication). Hence, the method also allows to reduce power consumption of the BTE device of the invention.

Furthermore, in case that forward communication takes place over the magnetic induction link only, an upper RF band receiver is not required on the BTE device. In case that backward communication takes place over the electromagnetic field propagation link only, a magnetic induction transmitter is not required on the BTE device. This allows to save space on the BTE device.

Primary benefits of different embodiments of the present invention may or may not include:

One and the same coil is used for two simultaneous links of different type.

Two antennas integrated in one component, this saves space.

Additional electrical RF isolation between diplexer transceiver ports is obtained due to common and differential mode operation.

Band diplexer contains physical small surface mount (SMT) elements, since the capacitor and inductance values are very small, e.g. 10 pF and 100 nH for lumped elements.

Implanted battery can be charged over the lower RF band simultaneously in time with a bidirectional communication link in the upper RF band.

Coexistence and simultaneous operation between the existing 5 MHz power/data link and any other wireless external devices.

Magnetic induction technology is most optimized for power transfer towards the implant and bidirectional communication links ranging 30 cm or shorter, whereas electromagnetic bidirectional communication links reaches ranges of several meters.

In certain aspects, an active implantable medical device (100) comprising an antenna (1160) and a band diplexer (1140) connected to the antenna is provided. The band diplexer comprises first filter means (1141, 1142) for.: a first signal to be transmitted and/or received in a first RF band and second filter means (1144) for a second signal to be transmitted and/or received in a second RF band, the second RF band being higher in frequency than the first RF band. In further aspects, the antenna comprises one or multiple windings. In further aspects, the first signal is applied to the antenna in differential mode and the second signal is applied to the antenna in common mode. In further aspects, the antenna is arranged to transmit and/or receive the first signal over an MI near-field and arranged to transmit and/or receive the second signal over a radiating near-field or EM far-field. In further aspects, the antenna is arranged to operate simultaneously for transmitting or receiving the first signal and transmitting or receiving the second signal. In further aspects, a first device (1130) is arranged to receive the first signal in the first RF band and connected to the band diplexer, and a second device (1110) is arranged to transmit the second signal in a second RF band and connected to the band diplexer. In further aspects, the first device is connected to the band diplexer in differential mode and the second device is connected to the band diplexer in common mode. In further aspects, the first device (1130) is further arranged for transmitting in the first RF band; and the second device (1110) is further arranged for receiving in the second RF band. In further aspects, both the first and the second devices are arranged for transferring unidirectionally power from the antenna towards the active implantable medical device using the reactive near field. In further aspects, the frequencies of the first RF band are below or equal to 30 MHz and the frequencies of the second RF band are above 30 MHz. In further aspects, the first signal is analogue and/or digital and the second signal is analogue and/or digital. In further aspects, an antenna matching unit (1120) is arranged for impedance matching of the antenna (1160) to an open-ended antenna for operation in the second RF band, wherein the antenna matching unit is connected to the band diplexer. In further aspects, the first and/or second signal comprises one or more data from the group consisting of: telemetry, control data, signaling data and audio streaming. In further aspects, the active implantable medical device is a cochlear implant.

In certain aspects, external hearing aid device comprising an antenna system (1480) and a band diplexer (2140) connected to the antenna system is provided. The band diplexer comprises first filter means for a first signal to be transmitted and/or received in a first RF band and second filter means for a second signal to be transmitted and/or received in a second RF band, the second RF band being higher in frequency than the first RF band. In further aspects, the antenna system comprises a closed-wire antenna. In further aspects, the first signal is applied to the antenna in differential mode and the second signal is applied to the antenna in common mode. In further aspects, the hearing aid system comprises a cochlear implant and one or more external devices. In further aspects, the one or more external devices comprise a sound processor device for behind the ear (1401). In further aspects, the sound processor device for behind the ear comprises a connector for a closed-wire antenna (470) external to the device for behind the ear for transcutaneous power transfer to the cochlear implant. In further aspects, the one or more external devices comprise a device for in the ear canal of a recipient. In further aspects, the one or more external devices comprise a remote control or handheld device.

In certain aspects, a method of bidirectional wireless communication between an active implantable medical device and an external device is provided. The method comprises the steps of: communicating unidirectionally from the external device to the implantable medical device over a first wireless link in a first RF band in the MI near-field and communicating unidirectionally from the implantable medical device to the external device over a second wireless link in a second RF band in the EM-field.

In certain aspects, a method of bidirectional wireless communication between an external hearing aid device and a second external device is provided. The method comprises the steps of: communicating unidirectionally from the second external device to the external hearing aid device over a first wireless link in a first RF band in the MI near-field and communicating unidirectionally from the external hearing aid device to the second external device over a second wireless link in a second RF band in the EM-field. In further aspects, the second RF band is higher in frequency than the first RF band.

What is claimed:
1. A hearing aid device comprising:
   a housing configured to be worn behind a first ear of a recipient;
   at least one microphone positioned next to an opening in the housing;
   a signal processor positioned in the housing and configured to receive an audio stream from the microphone;
   a first transceiver positioned in the housing and a first antenna electrically connected to the first transceiver, wherein the first transceiver and the first antenna are configured to generate a near-field link that extends from a first side of the recipient's head to a contralateral second side of the recipient's head; and
   a second transceiver positioned in the housing and a second antenna electrically connected to the second transceiver, wherein the second transceiver and the second antenna are configured to generate a far-field link in the ultra-high frequency band.

2. The hearing aid device of claim 1, wherein the first transceiver and the first antenna are configured to establish a binaural communications link with a contralateral hearing aid device via the near-field link.

3. The hearing aid device of claim 1, further comprising:
   an in-the-ear speaker configured to be worn in an ear canal of the recipient; and a lead electrically connected to the in-the-ear speaker to conduct audio signals from the signal processor to the in-the-ear speaker, wherein the second transceiver and the second antenna are coupled to the lead and the lead is configured to function as a radiating antenna.

4. The hearing aid device of claim 1, further comprising:
an in-the-ear speaker configured to be worn in an ear canal of the recipient; and
a lead electrically connected to the in-the-ear speaker to conduct audio signals from the signal processor to the in-the-ear speaker.

5. The hearing aid device of claim 4, wherein the lead is configured to operate as an extension of the second antenna coupled to the second transceiver.

6. The hearing aid device of claim 1, wherein the first transceiver and the first antenna are configured to communicate audio from the at least one microphone to a contralateral hearing aid device via the near-field link.

7. The hearing aid device of claim 1, wherein the first transceiver and the first antenna are configured to operate in a first Radio Frequency (RF) band using magnetic induction and the second transceiver and the second antenna are configured to operate in a second RF band using electromagnetic field propagation simultaneously in time.

8. The hearing aid device of claim 1, wherein the second transceiver and the second antenna are configured to stream audio from a handheld device via the far-field link.

9. A hearing aid system comprising:
the hearing aid device of claim 1; and
a contralateral hearing aid device configured to be worn behind a second ear of the recipient on the contralateral second side of the recipient's head, the contralateral hearing aid device comprising a third transceiver and a third antenna configured to enable communication with the hearing aid device over the near-field link,
wherein the near-field link comprises a binaural communications link.

10. The hearing aid system of claim 9, wherein the first transceiver and the first antenna and the third transceiver and the third antenna are configured to operate the binaural communications link at an operating frequency that is less than 30 megahertz (MHz).

11. The hearing aid system of claim 9, wherein the first transceiver and the first antenna and the third transceiver and the third antenna are configured for near field communication in the first RF band using magnetic induction.

12. The hearing aid system of claim 9, wherein the first antenna and the third antenna are each coil antennas.

13. The hearing aid system of claim 12, wherein the coil antennas coupled to the first transceiver and the third transceiver are each closed-wire loop antennas.

14. The hearing aid system of claim 9, wherein the contralateral hearing aid device comprises a fourth transceiver and a fourth antenna configured to generate a far-field link in the ultra-high frequency band.

15. The hearing aid system of claim 14, wherein the second antenna and the fourth antenna are radiating antennas.

16. The hearing aid system of claim 15, wherein the radiating antennas coupled to the second transceiver and the fourth transceiver are each dipole antennas.

17. The hearing aid system of claim 15, wherein the radiating antennas coupled to the second transceiver and the fourth transceiver are each open-ended wire antennas.

18. The hearing aid system of claim 14, further comprising:
a remote device comprising a fifth transceiver and a fifth antenna configured to generate a far-field link in the ultra-high frequency band,
wherein the second transceiver and the second antenna, the fourth transceiver and the fourth antenna, and the fifth transceiver and the fifth antenna are configured to operate the far-field link at an operating frequency of 2.4 Gigahertz (GHz).

* * * * *